(12) United States Patent
Hama et al.

(10) Patent No.: US 8,948,464 B2
(45) Date of Patent: Feb. 3, 2015

(54) BIOMETRIC AUTHENTICATION DEVICE AND BIOMETRIC AUTHENTICATION METHOD

(75) Inventors: Soichi Hama, Kawasaki (JP); Takahiro Aoki, Kawasaki (JP); Mitsuaki Fukuda, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 579 days.

(21) Appl. No.: 13/160,919

(22) Filed: Jun. 15, 2011

(65) Prior Publication Data

US 2011/0243396 A1   Oct. 6, 2011

Related U.S. Application Data

(63) Continuation of application No. PCT/JP2008/072973, filed on Dec. 17, 2008.

(51) Int. Cl.
G06K 9/00 (2006.01)
A61B 5/117 (2006.01)

(52) U.S. Cl.
CPC ..................................... A61B 5/117 (2013.01)
USPC ....................................................... 382/115

(58) Field of Classification Search
CPC ..................................................... A61B 5/117
USPC ............................................... 382/115, 124
See application file for complete search history.

(56) References Cited

U.S. PATENT DOCUMENTS

| 5,077,803 | A | 12/1991 | Kato et al. |
| 6,404,904 | B1 | 6/2002 | Einighammer et al. |
| 6,537,225 | B1 | 3/2003 | Mills |
| 2002/0188205 | A1 | 12/2002 | Mills |
| 2003/0012413 | A1 | 1/2003 | Kusakari et al. |
| 2003/0109772 | A1 | 6/2003 | Mills |

(Continued)

FOREIGN PATENT DOCUMENTS

| JP | 01-233556 | 9/1989 |
| JP | 02-079181 | 3/1990 |

(Continued)

OTHER PUBLICATIONS

International Search Report for PCT/JP2008/072973, Mailed Mar. 17, 2009.

(Continued)

*Primary Examiner* — Samir Ahmed
(74) *Attorney, Agent, or Firm* — Staas & Halsey LLP

(57) ABSTRACT

A biometric authentication device is provided with an input section for inputting identification information relative to a user, an imaging section which captures images of a hand of the user a plurality of times; a matching section which extracts vein information from each image of the hand captured by the imaging section and collates the vein information with prepared vein data corresponding to the identification information; a judgment data generation section which obtains data for judgment indicating whether the image of the hand is obtained by capturing the images of a living body, on the basis of the image of the hand; and a judgment section which authenticates the user when the result of the matching by the matching section relative to each image of the hand indicates normality and the data for judgment indicates that the image of the hand is obtained by imaging the living body, but which otherwise does not authentication the user.

9 Claims, 18 Drawing Sheets

(56) References Cited

U.S. PATENT DOCUMENTS

| | | |
|---|---|---|
| 2004/0162493 A1 | 8/2004 | Mills |
| 2005/0177046 A1 | 8/2005 | Mills |
| 2007/0092115 A1* | 4/2007 | Usher et al. .................. 382/117 |
| 2008/0118114 A1* | 5/2008 | Takiguchi ..................... 382/124 |
| 2008/0181466 A1* | 7/2008 | Iizuka et al. .................. 382/115 |
| 2008/0285812 A1* | 11/2008 | Rensen et al. ................ 382/115 |
| 2010/0191080 A1 | 7/2010 | Mills |
| 2010/0215223 A1 | 8/2010 | Abe |
| 2011/0025835 A1* | 2/2011 | Higuchi ........................... 348/77 |

FOREIGN PATENT DOCUMENTS

| | | |
|---|---|---|
| JP | 2000-005148 | 1/2000 |
| JP | 2002-513188 | 5/2002 |
| JP | 2003-030659 | 1/2003 |
| JP | 2003-511101 | 3/2003 |
| JP | 2003-331268 | 11/2003 |
| JP | 3721165 | 9/2005 |
| JP | 2004-215807 | 11/2005 |
| JP | 2007-037652 | 2/2007 |
| JP | 2007-122237 | 5/2007 |
| JP | 2008-099783 | 5/2008 |
| JP | 2008-148862 | 7/2008 |
| JP | 2008-287433 | 11/2008 |

OTHER PUBLICATIONS

English Translation of the International Preliminary Report on Patentability mailed Jul. 14, 2011 in corresponding International Patent Application PCT/JP2008/072973.

Japanese Notice of Reason for Rejection mailed Nov. 27, 2012 issued in corresponding Japanese Patent Application No. 2010-542781.

\* cited by examiner

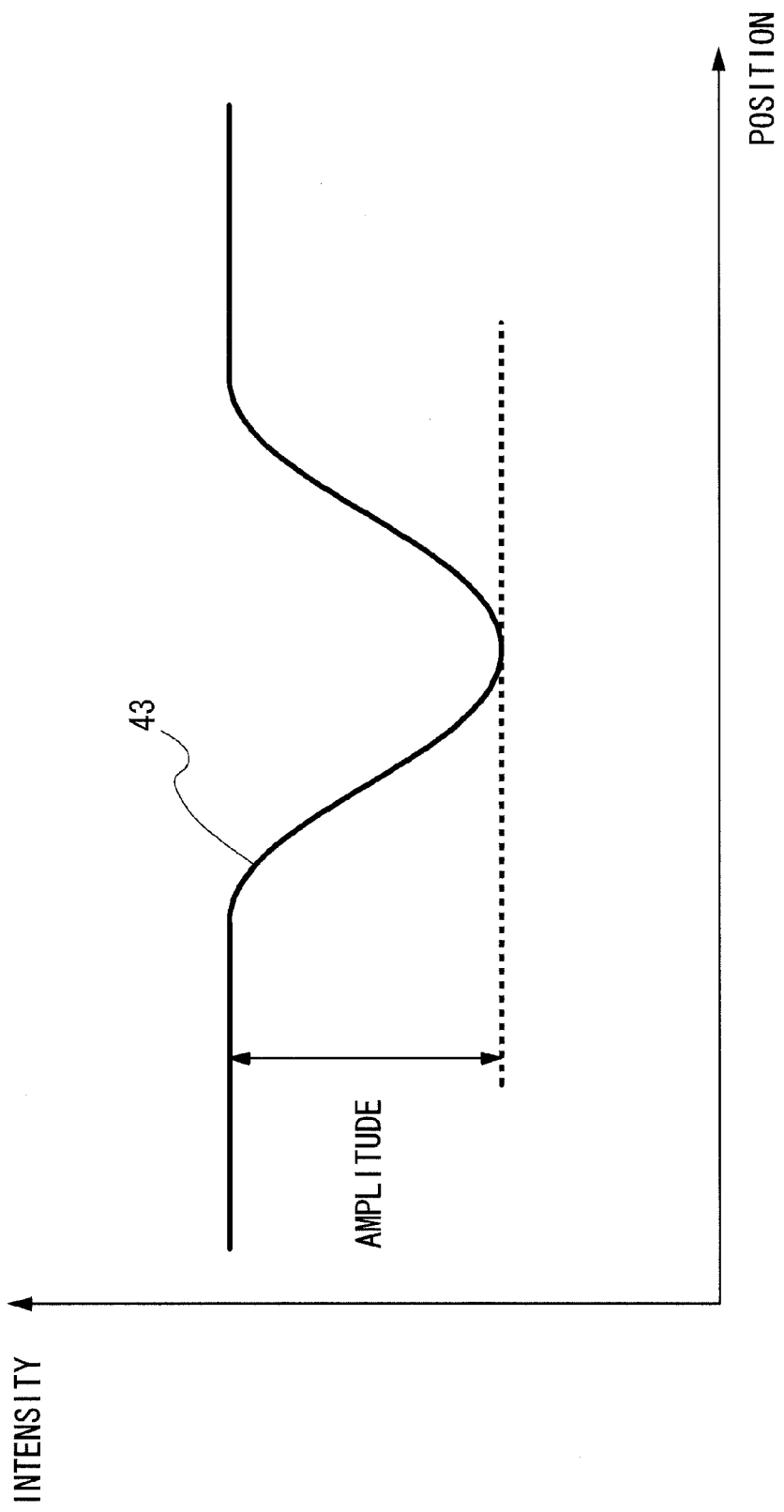

BIOMETRIC AUTHENTICATION DEVICE AND BIOMETRIC AUTHENTICATION METHOD

CROSS-REFERENCE TO RELATED APPLICATIONS

This is a continuation of Application, filed under 35 U.S.C. §111 (a) of International Application PCT/JP2008/072973, filed on Dec. 17, 2008, the contents of which are herein wholly incorporated by reference.

FIELD

The present invention relates to a biometric authentication device. The present invention can be applied to, e.g., biometric authentication using veins.

BACKGROUND

A biometric authentication technology is a technology of confirming an identity from biometric features such as a fingerprint, a face, an iris, a voiceprint and handwriting.

The biometric authentication technology involves utilizing the biometric features indispensable for the identity and is therefore considered low in terms of a risk of being stolen and faked as compared with an identity check based on storage of a personal identification number and a password and an identity check based on a seal and a card. A possibility of "spoofing" is, however, pointed out, which establishes the authentication in such a way that a third party acquires the biometric feature in an unauthorized manner and uses a copy of the biometric feature as a fake.

For example, there is a technology of determining whether the target body is the living organism or not by measuring an electrical characteristic of a skin. Further, another technology is that whether the target body is the living organism or not is determined by optically detecting that the skin is multilayer-structured or detecting a color of the skin. Still another technology is proposed, which determines from a pulse wave whether the target body is the living organism or not.

Alternatively, as by a technology of making the determination from a motion of a pupil upon which the light impinges, a technology exists, which determines based on a response to an external stimulus whether the target body is the living organism or not. Further, there is a technology of determining whether the target body is the living organism or not by heating or cooling a finger after being authenticated and detecting an expansion or contraction of arteriovenous anastomosis.

[Patent document 1] Japanese Patent Publication No. 3721165
[Patent document 2] Japanese Patent Laid-Open Publication No. 2008-99783
[Patent document 3] Japanese Patent Laid-Open Publication No. H02-079181
[Patent document 4] Japanese Unexamined Patent Publication No. 2002-513188
[Patent document 5] Japanese Patent Laid-Open Publication No. 2007-122237
[Patent document 6] Japanese Patent Laid-Open Publication No. 2003-331268
[Patent document 7] Japanese Patent Laid-Open Publication No. 2008-148862
[Patent document 8] Japanese Patent Laid-Open Publication No. 2003-30659
[Patent document 9] Japanese Patent Laid-Open Publication No. 2007-37652

SUMMARY

It is desirable for realizing a high security level through the biometric authentication to precisely determine whether the target body observed to acquire the feature is the living organism or the fake.

The present invention aims at providing a biometric authentication device capable of enhancing the accuracy of the biometric authentication.

According to one mode of the present invention, a biometric authentication device includes: an input unit to input identifying information of a user; an image capturing unit to capture an image of a user's hand a plural number of times; a authentication unit to extract vein information, on a per image basis, of the hand image captured by the image capturing unit and execute a matching process of the vein data with previously-provided vein data associated with the identifying information; a determination data generation unit to acquire determination data specifying based on the hand image whether the hand image is acquired by capturing the living organism or not; and a determination unit to authenticate the user if a matching result of the matching unit on the per hand-image basis demonstrates its normality and if the determination data demonstrates that the hand image is acquired by capturing the living organism, and to authenticate none of the user whereas if not.

According to the biometric authentication device, the accuracy of the biometric authentication can be enhanced.

BRIEF DESCRIPTION OF THE DRAWINGS

FIG. 18 is an explanatory diagram of the calculation method of the thickness of the blood vessel of the vein by use of an amplitude.

Figure 1:
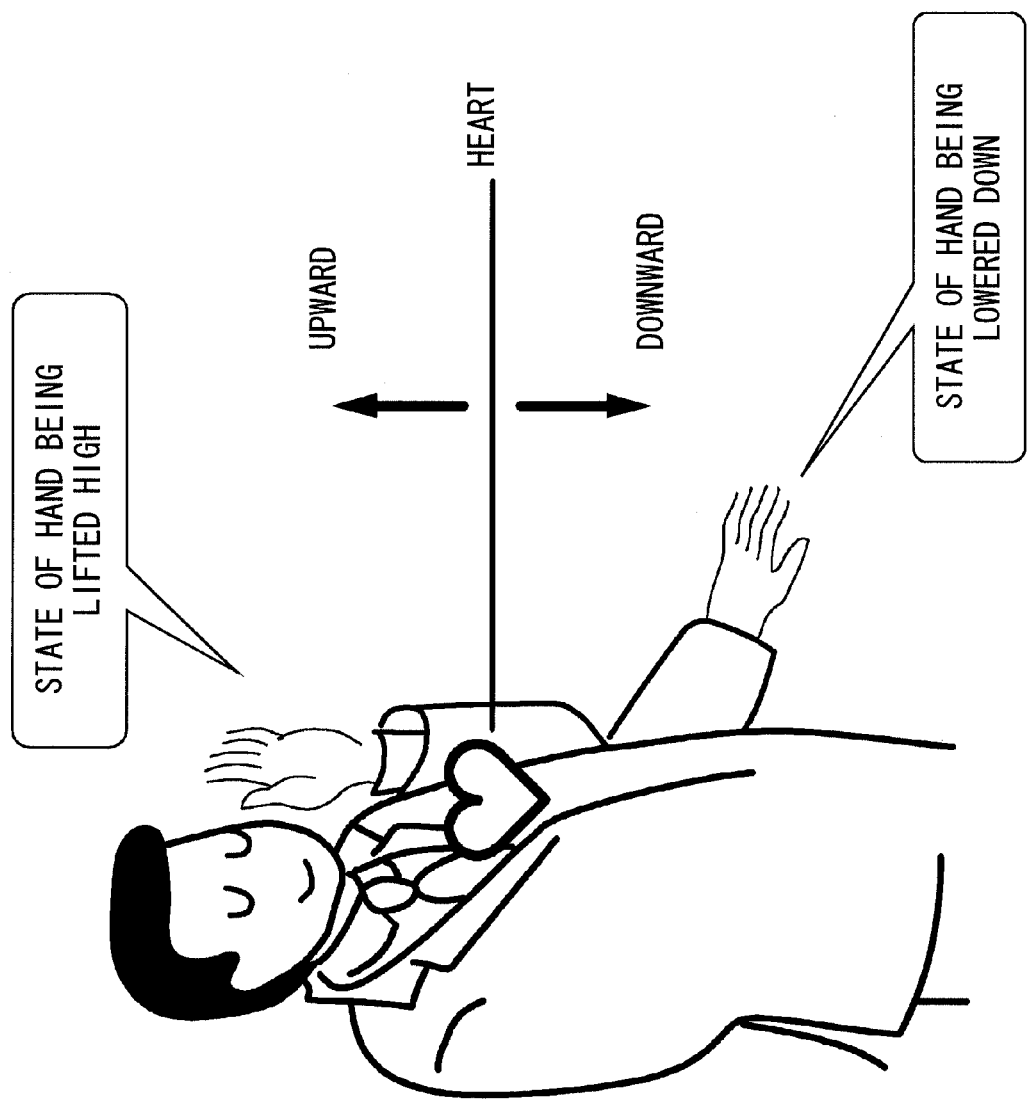
FIG. 1 is a view illustrating an example of a relation between a position of a heart and a position of a hand.

REFERENCE SIGNS LIST 100 biometric authentication device
102 vein sensor unit
104 operation unit
106 image capturing unit
110 liveness detection unit
112 aligning and thickness measuring unit
114 thickness information collecting unit
120 vein authentication unit
122 vein pattern extracting unit
124 vein pattern matching unit
126 storage unit
130 determination unit

DESCRIPTION OF EMBODIMENTS

An embodiment of a biometric authentication device will hereinafter be described with reference to the drawings. A configuration in the following embodiment is an exemplification, and the present invention is not limited to the configuration in the embodiment of the disclosure.

Herein, the discussion will deal with mainly veins of a palm of a hand, however, the veins of regions (parts) such as fingers of the hand other than the palm can be similarly applied.

Embodiment

Outline

The configuration of the embodiment realizes a vein authentication and a liveness detection simultaneously by utilizing such a point that a thickness of a blood vessel changes as a blood pressure varies. The liveness detection connotes determining whether a measurement target body is classified as a living organism or a fake.

Figure 2:
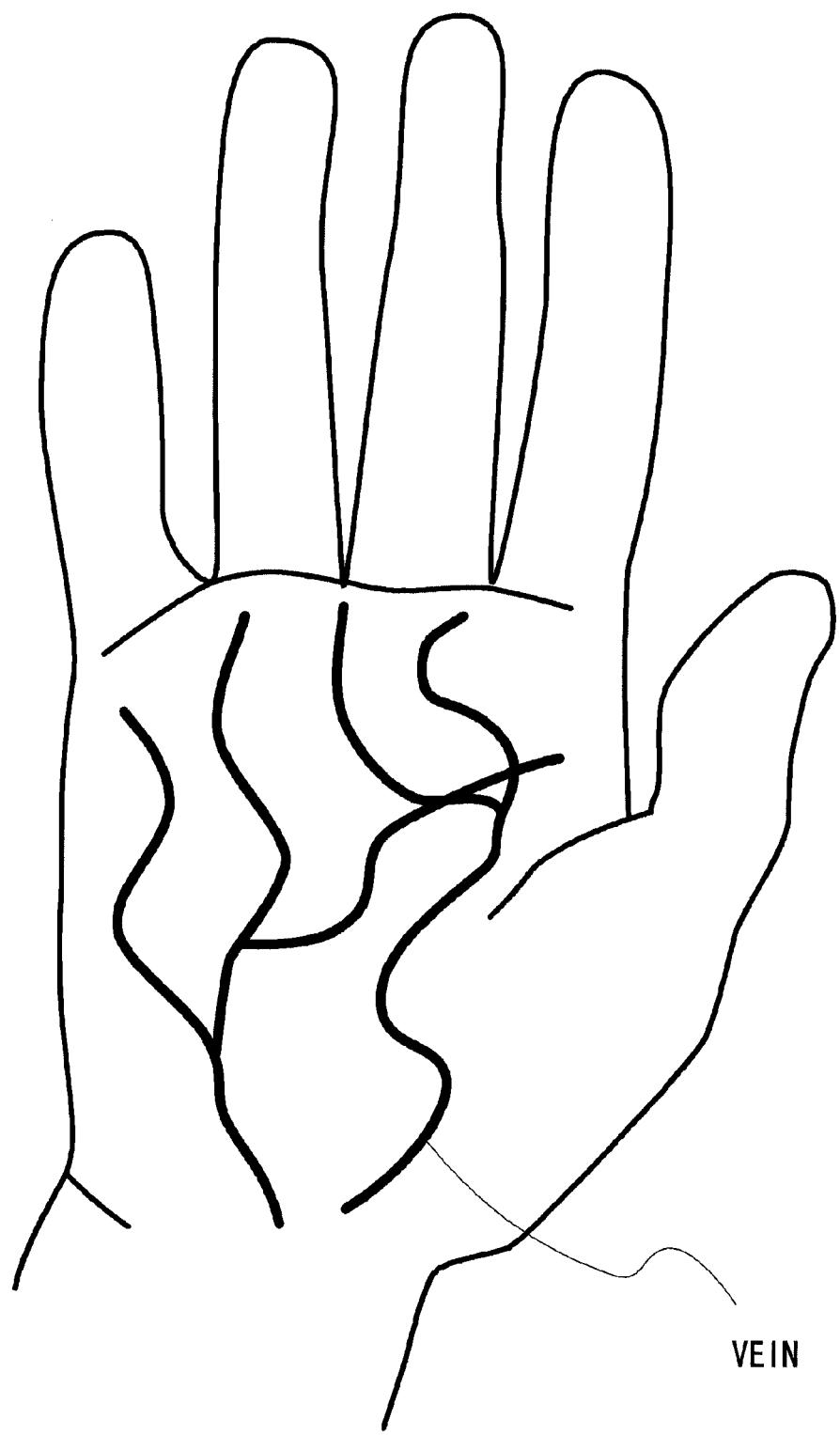
FIG. 2 is a view illustrating an example of the hand and veins of a palm.
Figure 3:
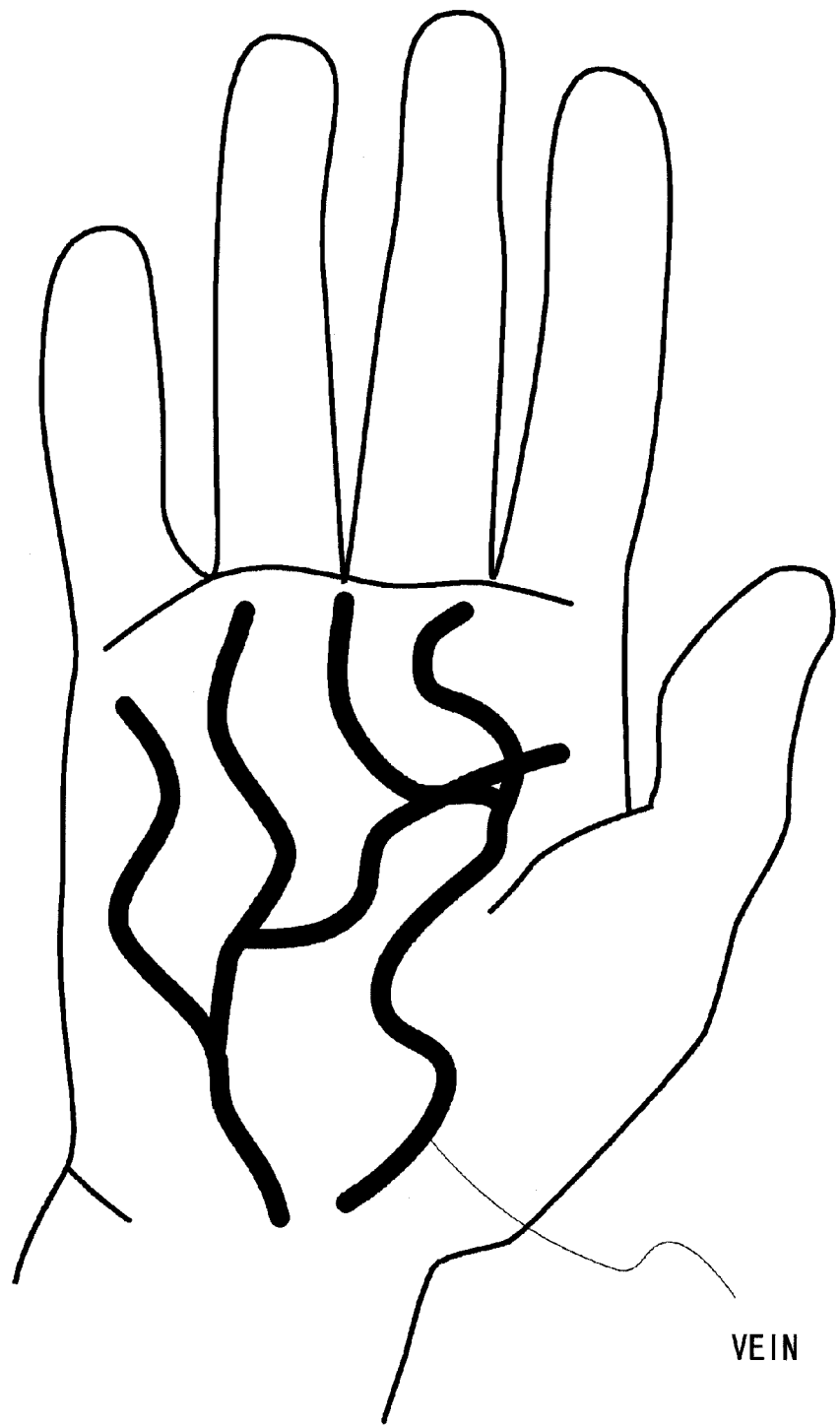
FIG. 3 is a view illustrating an example of the hand and veins of a palm.

FIG. 1 is a view illustrating an example of a relation between a position of a heart and a position of the hand. FIGS. 2 and 3 are views each illustrating an example of the hand and the veins of the palm. FIG. 2 is the view depicting the example of the hand and the veins of the palm when the hand is lifted higher than the heart. FIG. 3 is the view depicting the example of the hand and the veins of the palm when the hand descends lower than the heart.

It is generally known that the blood pressure of the hand decreases when lifting the hand higher than the heart but increases when lowering the hand under the heart. At this time, the thickness of the blood vessel of the hand vein changes as the blood pressure of the hand varies. Namely, when comparing the thickness of the blood vessel of the hand vein in the case of raising the hand high in FIG. 2 with the thickness of the blood vessel of the hand vein in the case of lowering the hand down in FIG. 3, the thickness of the blood vessel of the hand vein in the case of raising the hand high is smaller. On the other hand, the hand vein (blood vessel) itself neither moves nor disappears. Namely, when making a comparison between a vein pattern (a layout of the blood vessels of the veins) of the hand in the case of lifting the hand high in FIG. 2 and the vein pattern of the hand in the case of lowering the hand in FIG. 3, these vein patterns of the hand are the same.

Thus, the thickness of the blood vessel of the vein changes by artificially causing the variation of the blood pressure. It is, however, considered that an artificially produced fake vein undergoes no change of the blood vessel of the vein. Such being the case, it is feasible to determine whether the measurement target body is the living organism or the fake by measuring the thickness of the blood vessel of the vein in a manner that artificially changes the blood pressure of the hand.

Figure 4:
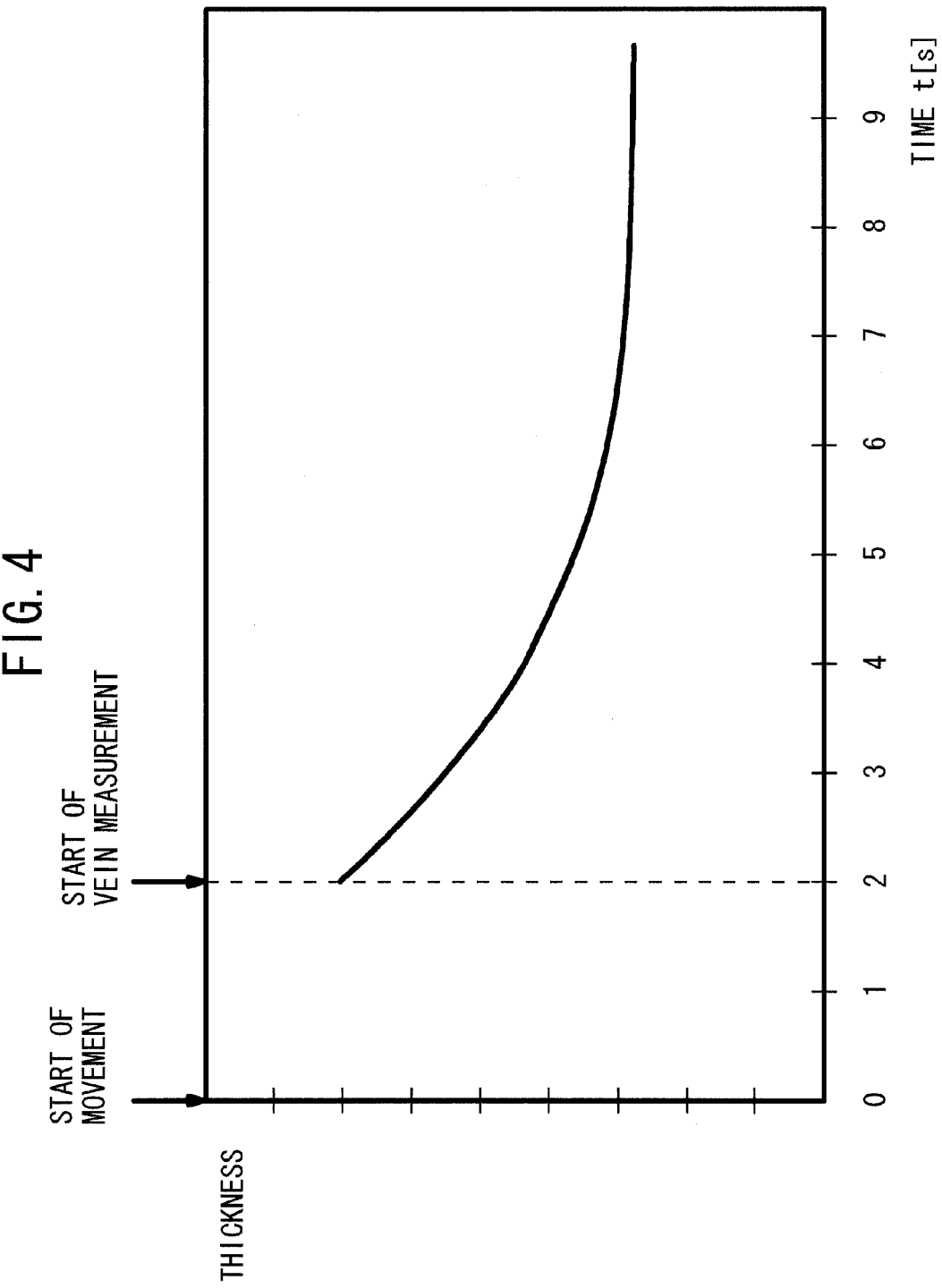
FIG. 4 is a diagram showing an example of a time-based variation of a thickness of the vein.

FIG. 4 is a graph illustrating an example of how the thickness of the blood vessel of the vein changes with the time. In the graph of FIG. 4, the axis of abscissa represents the time, and the axis of ordinates represents the thickness of the blood vessel of the vein. The thickness of the blood vessel of the vein is graphed based on actual measurements. The example of FIG. 4 shows a result of the measurement based on the following procedure.

(1) A user, whose thickness of the blood vessel of the vein is measured, stabilizes the user's own hand for at least 10 seconds or longer in a position lower than a vein sensor.

(2) Thereafter, the user moves the user's hand to above the vein sensor disposed in a position higher than the present position of the hand within a period from the time t=0 second to the time t=2 seconds.

(3) The vein sensor captures an image of the hand a predetermined number of times at an interval of 0.1 second since the time t=2 seconds. Thereafter, the thickness of the blood vessel of the vein at a specified point of the hand is measured on a per captured hand-image basis.

It is understood from the graph of the thickness of the blood vessel of the vein in FIG. 4 that the thickness of the blood vessel of the vein converges for the time t=7-8 seconds. Hence, the measurement is started since the time t=2 seconds, so that the time till the vein contraction is stabilized is on the order of 5-6 seconds. Accordingly, the thickness of the blood vessel of the vein is measured for approximately 5-6 seconds while holding the hand over the vein sensor, thereby enabling the measurement target body to be distinguished between the living organism and the fake.

Further, as obvious from the graph in FIG. 4, at ime-based variation of the thickness of the vein extremely increases immediately after starting the measurement. It is therefore possible to sufficiently make the distinction of the measurement target body between the living organism and the fake even by measuring the thickness of the blood vessel of the vein for 2-3 seconds since the hand has been held over the vein sensor.

The example in FIG. 4 demonstrates the time-based variation of the thickness of the vein just after lifting the hand kept in the low position up to the high position. The time-based variation of the thickness of the vein just after, conversely, lowering the hand kept in the high position down to the low position is the same as in the example of FIG. 4. In this case, however, the value of the thickness of the blood vessel of the vein increases on a step-by-step basis and thus converges.

Example of Configuration

Figure 5:
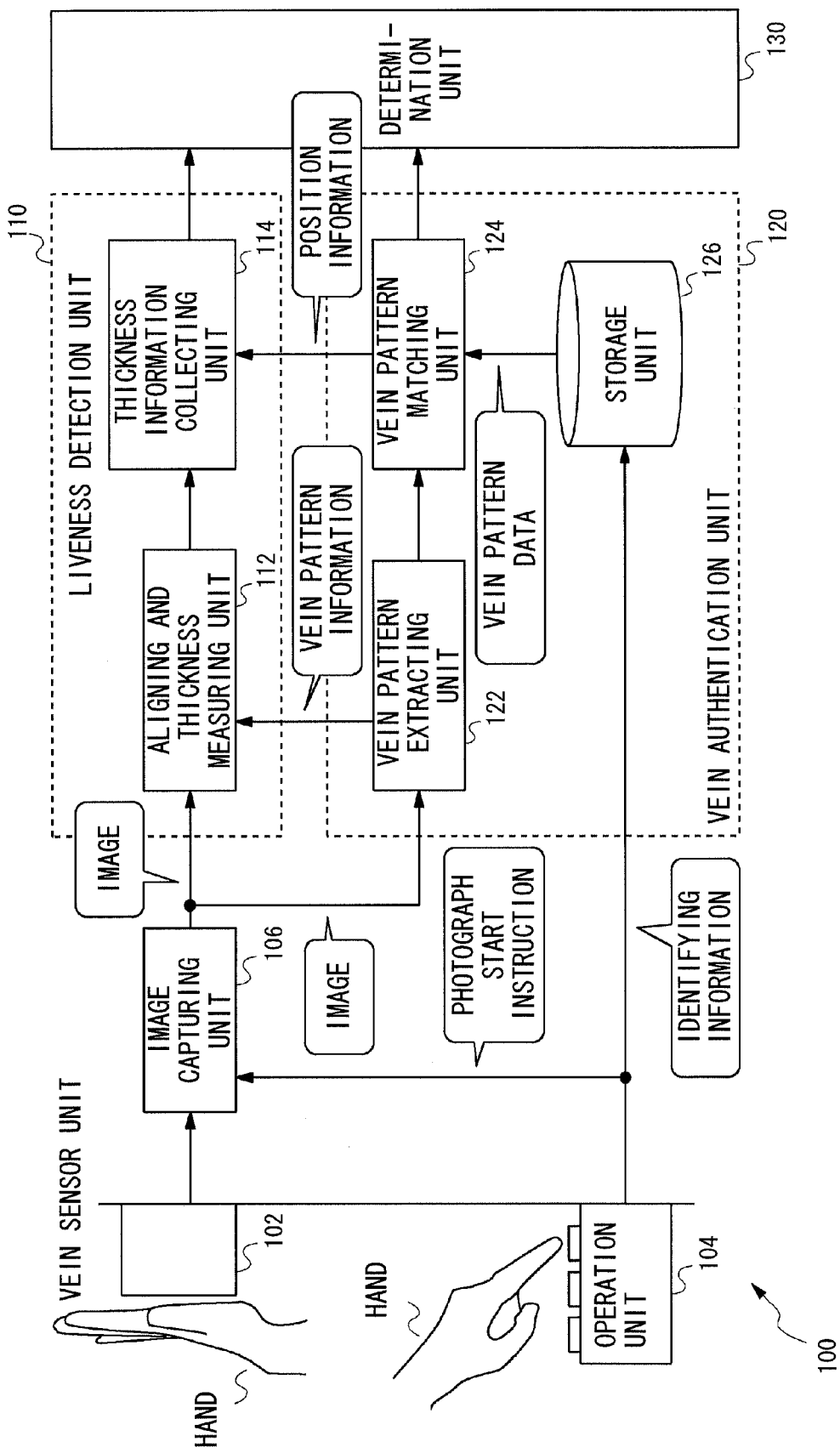
FIG. 5 is a diagram illustrating an example of a configuration of a biometric authentication device.

FIG. 5 is a diagram illustrating an example of a configuration of the biometric authentication device according to the embodiment.

A biometric authentication device 100 in FIG. 5 includes a vein sensor unit 102, an operation unit 104, an image capturing unit 106, a liveness detection unit 110, a vein authentication unit 120 and a determination unit 130. The liveness detection unit 110 includes an aligning and thickness measuring unit 112 and a thickness information collecting unit 114. The vein authentication unit 120 includes a vein pattern extracting unit 122, a vein pattern matching unit 124 and a storage unit 126. Some of these plural blocks can be aggregated into one single block. Alternatively, at least one of the plurality of blocks can be further segmented into a plurality of sub-blocks.

The vein sensor unit 102 is equipped with a camera which captures the image of the palm held over the vein sensor unit 102 in accordance with an instruction of the image capturing unit 106. The vein sensor unit 102 captures the images of the palm at least twice on the basis of the instruction of the image capturing unit 106. Capturing a plural number of times intends to observe the time-based variation of the thickness of the vein. The vein sensor unit 102 can capture the veins of the palm.

The operation unit 104 accepts an input of user's identifying information such as a user's ID number from the user. The operation unit 104 can be constructed of an operation panel like, e.g., a keyboard, a touch panel and a card reader.

The operation unit 104 is installed in a position lower than a position of the vein sensor unit 102. The operation unit 104 can be installed in the position lower than a position of a heart of the user. The vein sensor unit 102 can be installed in a position higher than the position of the heart of the user. Further, the operation unit 104 may also be installed in the position higher than the position of the vein sensor unit 102. A reason why the vein sensor unit 102 is installed with the height different from the height of the operation unit 104 lies in causing a blood pressure difference between a blood pressure of the hand when user operates the operation unit 104 and a blood pressure of the hand when holding the hand over the vein sensor unit 102. In the example of FIG. 5, the operation unit 104 is installed in the position lower than the position of the vein sensor unit 102.

The operation unit 104 outputs the identifying information to the storage unit 126. Further, the operation unit 104 notifies the image capturing unit 106 that the operation unit 104 is operated by the user etc. This notification can serve as a capturing start instruction given to the image capturing unit 106.

The image capturing unit 106 instructs the vein sensor unit 102 to capture an image of the palm held over the vein sensor unit 102. The image capturing unit 106 can record a period of image capturing time. The image capturing unit 106 inputs the image captured by the vein sensor unit 102 to the liveness detection unit 110 and the vein authentication unit 120. The image capturing unit 106 can include an indicator for indicating the user, who has operated the operation unit 104, to hold the hand over the vein sensor unit 102.

The vein sensor unit 102 and the image capturing unit 106 can be configured into one single unit.

The liveness detection unit 110 acquires information for determining whether the measurement target body is the living organism or the fake, and outputs the thus-acquired information to the determination unit 130.

The aligning and thickness measuring unit 112 of the liveness detection unit 110 acquires, from the image capturing unit 106, the image of the palm, which is captured by the vein sensor unit 102. The aligning and thickness measuring unit 112 acquires vein pattern information from the vein pattern extracting unit 122 of the vein authentication unit 120. The aligning and thickness measuring unit 112 aligns the image acquired from the image capturing unit 106 with the vein pattern information obtained from the vein pattern extracting unit 122. The aligning and thickness measuring unit 112 determines a position of measuring the thickness of the blood vessel of the vein. The aligning and thickness measuring unit 112 can determine a plurality of positions of measuring the thickness of the blood vessel of the vein.

The aligning and thickness measuring unit 112 determines, as a thickness measuring point, a point becoming a midpoint of a specific line segment partly configuring the vein pattern from, e.g., the vein pattern information. Further, the aligning and thickness measuring unit 112 measures the thickness of the blood vessel of the vein in a direction orthogonal to a direction of the line segment via the midpoint by use of the image acquired from the image capturing unit 106. The point and the direction of measuring the thickness of the blood vessel of the vein and a method of calculating the thickness of the blood vessel of the vein, will hereinafter be described in detail. The aligning and thickness measuring unit 112 outputs one or more measuring points and the information on the thickness of the blood vessel of the vein in the position corresponding to the measuring point to the thickness information collecting unit 114.

The thickness information collecting unit 114 of the liveness detection unit 110 obtains, based on the information inputted from the aligning and thickness measuring unit 112, an average of the thicknesses of the blood vessels of the veins, and corrects a value of the thickness of the blood vessel of the vein by acquiring the position information from the vein pattern matching unit 124. The position information contains size information and gradient information of the hand of the image-captured vein pattern information about the vein having vein pattern data registered on the storage unit 126. The thickness information collecting unit 114 acquires the position information from the vein pattern matching unit 124 on a per captured-image basis as well as from the aligning and thickness measuring unit 112.

The vein sensor unit 102 captures the image of the palm in a non-contact state between the vein sensor unit 102 and the hand to be captured, in which case a distance between the vein sensor unit 102 and the hand to be captured is not necessarily fixed. Moreover, when the vein sensor unit 102 captures the image of the palm, a gradient of the capturing target hand to the vein sensor unit 102 is not necessarily fixed. Therefore, the thickness information collecting unit 114 corrects the thickness of the blood vessel of the vein by use of a ratio of the vein size of the vein pattern data registered on the storage unit 126 to the vein size of the image-captured vein pattern information and by use of the gradient information of the image-captured vein pattern with respect to the vein having the vein pattern data registered on the storage unit 126. This contrivance enables the thickness information collecting unit 114 to eliminate influence caused by a distance difference and a gradient difference between the vein sensor unit 102 and the hand to be captured from the thickness information of the blood vessel of the vein and the position information of the measuring point of the thickness of the blood vessel of the vein.

The vein authentication unit 120 compares the vein pattern information of the palm captured by the vein sensor unit 102 with the vein pattern data previously stored on the storage unit 126, and outputs a result of the comparison as a matching score. The matching score is a value indicating a degree of coincidence of the vein pattern information of the palm of the captured hand with the pre-stored vein pattern data. If the vein pattern information is completely coincident with the vein pattern data, the matching score takes a maximum value. The calculation of the matching score may involve using any types of methods.

The vein pattern extracting unit 122 acquires the image of the palm, which is captured by the vein sensor unit 102, from the image capturing unit 106. The vein pattern extracting unit 122 extracts the vein pattern of the palm from the image of the palm, and generates the vein pattern information. The vein pattern is defined as a layout of the blood vessels of the veins. The vein pattern information is what the vein pattern is abstracted.

Figure 6:
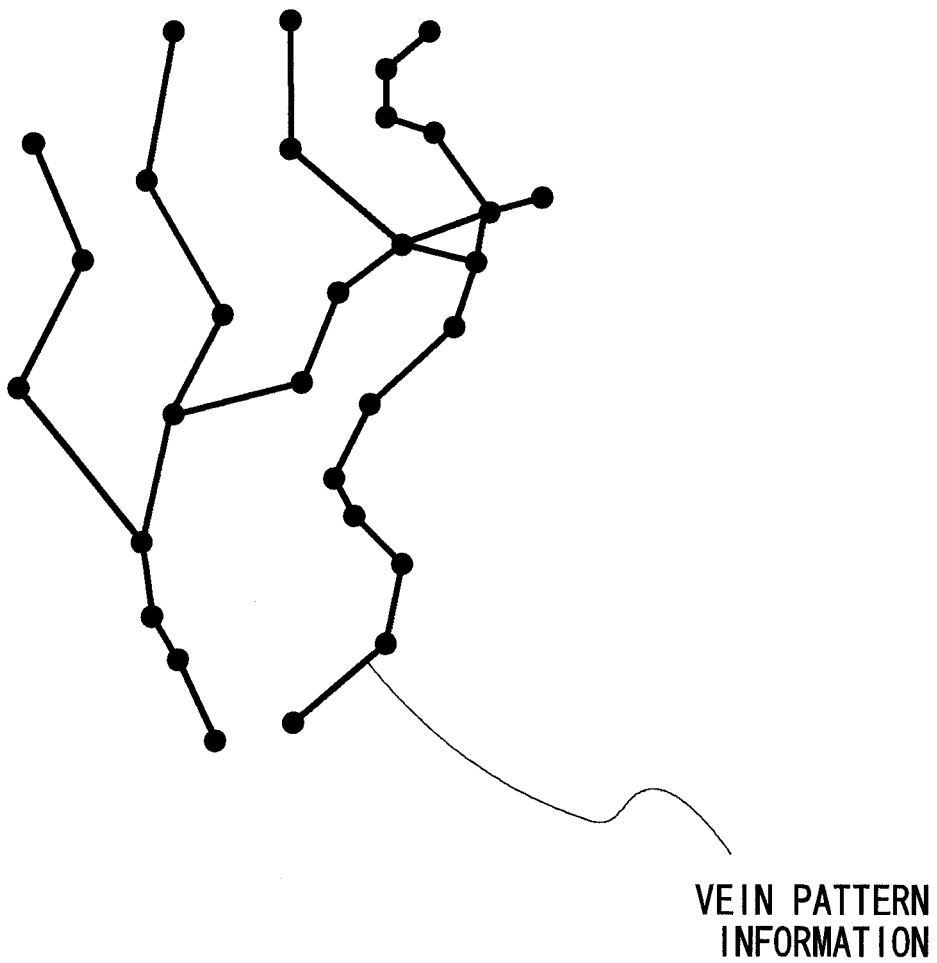
FIG. 6 is a diagram showing an example of vein pattern information.

FIG. 6 is a diagram depicting an example of the vein pattern information. The vein pattern information can be, as in FIG. 6, expressed by, e.g., an aggregation of the points on the blood vessels of the veins and straight lines which connect these points to each other. The points and the straight lines represent the veins. The vein pattern information may contain other categories of information excluding the point and the straight line.

The storage unit 126 is stored with the vein pattern information of the user. The vein pattern information of the user is registered beforehand on the storage unit 126. The vein pattern information registered on the storage unit 126 is also referred to as the vein pattern data. The storage unit 126 extracts the vein pattern data of the user on the basis of the user's authentication information inputted from the operation unit 104.

The vein pattern matching unit 124 calculates the matching score on the basis of the vein pattern information extracted by the vein pattern extracting unit 122 and the vein pattern data extracted from the storage unit 126. The vein pattern matching unit 124 outputs, to the thickness information collecting unit 114, the information on the ratio of the vein size of the vein pattern data extracted from the storage unit 126 to the vein size of the vein pattern information extracted by the vein pattern extracting unit 122. Further, the vein pattern matching unit 124 outputs, to the thickness information collecting unit 114, the vein gradient information of the vein pattern information extracted by the vein pattern extracting unit 122 with respect to the vein having the vein pattern data extracted from the storage unit 126. The vein pattern matching unit 124 outputs the thus-calculated matching score to the determination unit 130.

The value of the thickness of the blood vessel of the vein that is acquired by the liveness detection unit 110 and the matching score acquired by the vein authentication unit 120 are inputted on the per-captured-image basis to the determination unit 130. Further, the captured image is recorded with the capturing time. The capturing time information of the captured image is also inputted to the determination unit 130.

The determination unit 130 determines, based on the matching score obtained by the vein authentication unit 120, whether the vein pattern data extracted from the storage unit 126 is (identified with) the data of the user or not. Furthermore, the determination unit 130 determines, based on the value of the thickness of the blood vessel of the vein that is acquired by the liveness detection unit 110, the matching score acquired by the vein authentication unit 120 and the time information of the captured image, whether the captured palm is the living organism or not.

Operational Example

Operational Example of Whole

An outline of an operational example of the whole will be explained.

Figure 7:
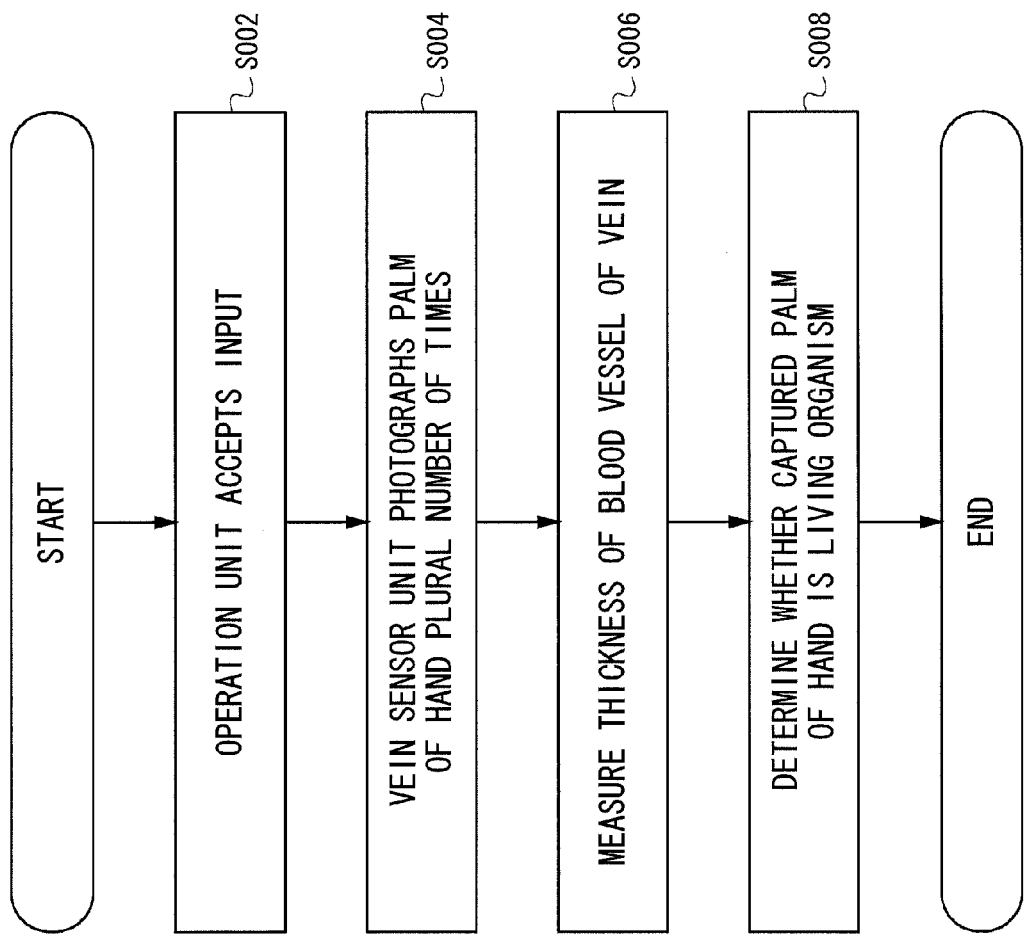
FIG. 7 is a flowchart showing an outline of an operational example of the whole.

FIG. 7 is a flowchart showing an outline of the operational example of the whole.

The operation unit 104 of the biometric authentication device 100 accepts an input of the manual operation of the user (S002). The operation unit 104 accepts the information (identifying information) for specifying the user. The information for specifying the user is inputted to the vein authentication unit 120. The operation unit 104, upon finishing the input to the operation unit 104 from the user, notifies the image capturing unit 106 of this purport.

The image capturing unit 106, when receiving from the operation unit 104 the notification purporting that the input to the operation unit 104 has been finished, instructs the user to hold the palm which manipulates the operation unit 104 over the vein sensor unit 102.

When the user holds the palm over the vein sensor unit 102 in response to the instruction of the image capturing unit 106, the image capturing unit 106 instructs the vein sensor unit 102 to capture the image of the palm of the user's handheld over the vein sensor unit 102. The image capturing unit 106 may also instruct the vein sensor unit 102 to start capturing after an elapse of a predetermined period of time since the instruction has been given.

The vein sensor unit 102 captures the image of the palm held over the vein sensor unit 102 in response to the instruction of the image capturing unit 106. The vein sensor unit 102 captures the palm at least twice in response to the instruction of the image capturing unit 106 (S004). The captured image is inputted to the liveness detection unit 110 and the vein authentication unit 120.

The vein authentication unit 120 extracts the vein pattern from the captured image and outputs the extracted vein pattern to the liveness detection unit 110. Further, the vein authentication unit 120 extracts, based on the information for specifying the user that is inputted from the operation unit 104, the user's vein pattern from the storage unit 126.

The vein authentication unit 120 compares the vein pattern extracted from the storage unit 126 with the vein pattern extracted from the captured image. The vein authentication unit 120 outputs the thus-matching result as the matching score to the determination unit 130. Moreover, the vein authentication unit 120 calculates the ratio of the vein size of the vein pattern extracted from the captured image to the vein size of the vein pattern extracted from the storage unit 126. Furthermore, the vein authentication unit 120 calculates the vein gradient information of the vein pattern information extracted from the captured image with respect to the vein having the vein pattern data extracted from the storage unit 126. The vein authentication unit 120 outputs this ratio and the gradient information as position information to the liveness detection unit 110.

The aligning and thickness measuring unit 112 of the liveness detection unit 110 determines the measuring point of the thickness of the blood vessel of the vein from the vein pattern information inputted from the vein authentication unit 120. The aligning and thickness measuring unit 112 aligns the captured image with the position of the vein pattern information, and thus determines the measuring point of the thickness of the blood vessel of the vein on the captured image. The aligning and thickness measuring unit 112 measures the thickness of the blood vessel of the vein at the measuring point determined on the captured image (S006). The direction of measuring the thickness of the blood vessel of the vein can be set in the direction orthogonal to the direction of the blood vessel of the vein.

The thickness information collecting unit 114 of the liveness detection unit 110 calculates, based on the measured thickness of the blood vessel of the vein and the position information inputted from the vein authentication unit 120, the thickness of the blood vessel of the vein on the per-captured-image basis. The thickness information collecting unit 114 outputs, to the determination unit 130, the thus-calculated thickness information of the blood vessel of the vein on the per-captured-image basis.

The determination unit 130 determines whether the target body captured by the vein sensor unit 102 is the living organism or not in a way that uses the thickness information of the blood vessel of the vein that is inputted from the liveness detection unit 110 and the matching score inputted from the vein authentication unit 120 (S008).

Operational Example of Aligning and Thickness Measuring Unit

The aligning and thickness measuring unit 112 acquires the image of the palm from the image capturing unit 106. The aligning and thickness measuring unit 112 acquires the vein pattern information from the vein pattern extracting unit 122. The aligning and thickness measuring unit 112 determines the measuring point of the thickness of the blood vessel of the vein by utilizing the vein pattern information. The aligning and thickness measuring unit 112 measures the thickness of the blood vessel of the vein at the thus-determined measuring point by use of the image of the palm. The aligning and thickness measuring unit 112 outputs the measured result to the thickness information collecting unit 114.

Figure 8:
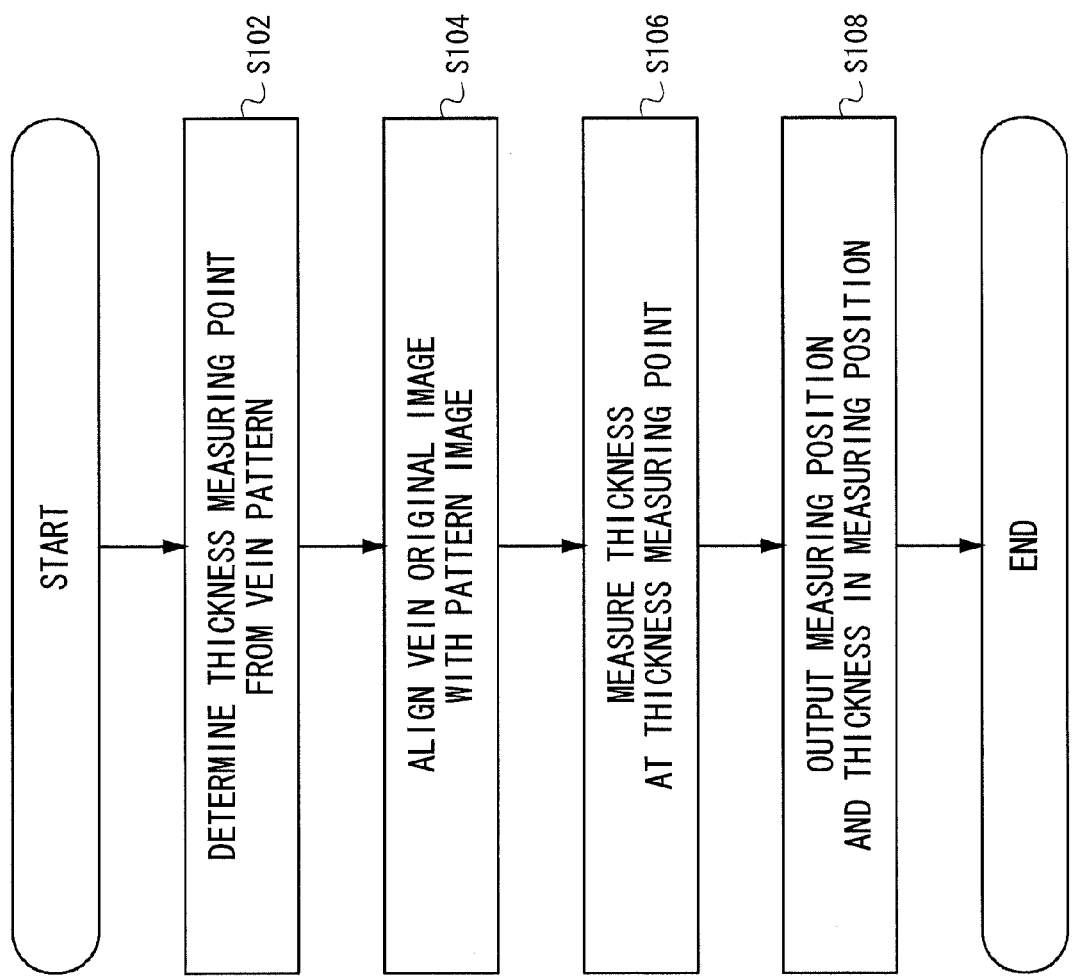
FIG. 8 is a flowchart showing an operational example of an aligning and thickness measuring unit.

FIG. 8 is a flowchart showing the operational example of the aligning and thickness measuring unit 112. The aligning and thickness measuring unit 112 acquires the image of the palm that is captured by the vein sensor unit 102 from the image capturing unit 106. Further, the aligning and thickness measuring unit 112 acquires the vein pattern information from the vein pattern extracting unit 122 of the vein authentication unit 120.

The aligning and thickness measuring unit 112 determines, as the measuring point of the thickness of the blood vessel of the vein, the midpoint of the specified line segment deemed to be the straight line in the veins configuring the vein pattern from the vein pattern information acquired from the vein pattern extracting unit 122 (S102). The aligning and thickness measuring unit 112 may determine otherwise the specified point on the vein pattern information as the measuring point of the thickness of the blood vessel of the vein. The aligning and thickness measuring unit 112 determines the measuring points of the thicknesses of the blood vessels of the plurality of veins.

The image acquired from the image capturing unit 106 is the information about the hand including the veins. On the other hand, the vein pattern information obtained from the vein pattern extracting unit 122 is the information on only the veins. Such being the case, the aligning and thickness measuring unit 112 aligns the image acquired from the image capturing unit 106 with the vein pattern information obtained from the vein pattern extracting unit 122 (S104). The aligning and thickness measuring unit 112 can, by performing the alignment, express an arbitrary position on the vein pattern information obtained from the vein pattern extracting unit 122 in the form of the position on the image acquired from the image capturing unit 106.

The aligning and thickness measuring unit 112 measures the thickness of the blood vessel of the vein in the direction orthogonal to the direction of the blood vessel of the vein at the determined measuring point by use of the image acquired from the image capturing unit 106 (S106). An in-depth description of the method of calculating the thickness of the blood vessel of the vein will hereinafter be made.

The aligning and thickness measuring unit 112 outputs, to the thickness information collecting unit 114, the position information at the plurality of measuring points and the information about the thickness of the blood vessel of the vein at the plurality of measuring points on the per-acquired-image basis from the image capturing unit 106 (S108).

Operational Example of Thickness Information Collecting Unit>

Figure 9:
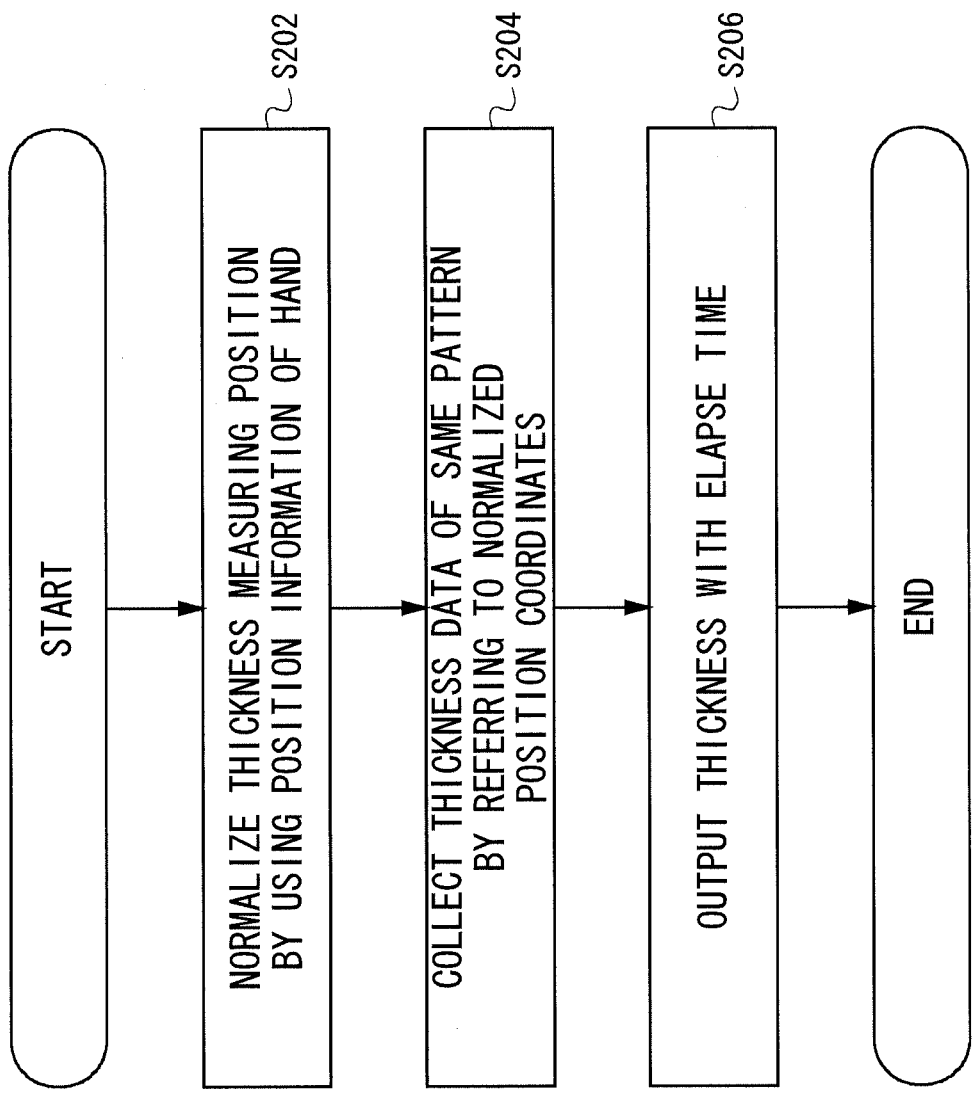
FIG. 9 is a flowchart showing an operational example of a thickness information collecting unit.

FIG. 9 is a flowchart showing an operational example of the thickness information collecting unit. The thickness information collecting unit 114 receives an input of the measured result of the thickness of the blood vessel of the vein from the aligning and thickness measuring unit 112.

A plurality of captured-images of the palm has a possibility that the sizes and the gradients of the palm might not be coincident with each other. This is because the hand held over the vein sensor unit 102 is not kept static when being captured. It is therefore necessary to normalize the sizes and the gradients of the images of the palm of the captured hand.

The thickness information collecting unit 114 acquires the position information on the per-captured-image basis from the vein pattern matching unit 124. The position information contains the ratio of the vein size of the vein pattern information extracted by the vein pattern extracting unit 122 to the vein size of the vein pattern data extracted from the storage unit 126. Further, the position information contains the vein gradient of the vein pattern information extracted by the vein pattern extracting unit 122 with respect to the vein having the vein pattern extracted from the storage unit 126.

The thickness information collecting unit 114 normalizes the measured result of the thickness of the blood vessel of the vein by use of the position information obtained from the vein pattern matching unit 124 (S202). Namely, the thickness information collecting unit 114 converts the thickness of the blood vessel and the position of the measuring point of the thickness of the blood vessel of the vein as the measured results into the thickness of the blood vessel and the position of the measuring point of the vein pattern information extracted from the storage unit 126. The normalization thereof enables the thickness information collecting unit 114 to compare the plurality of captured images of the palm with each other.

The thickness information collecting unit 114 extracts the measuring point of the thickness of the blood vessel of the vein that is common to all of the captured images. The thickness information collecting unit 114 extracts the thickness of the blood vessel of the vein at the extracted measuring point on the per-captured-image basis (S204). The thickness information collecting unit 114 calculates an average value of the plurality of extracted thicknesses of the blood vessels of the veins on the per-captured-image basis. The thickness information collecting unit 114 sets, if the single thickness of the blood vessel of the vein is extracted, a value of this thickness as the average value.

The thickness information collecting unit 114 outputs the average value of the thicknesses of the blood vessels of the veins to the determination unit 130 on the per-captured-image basis (S206). The information, which is output to the determination unit 130 from the thickness information collecting unit 114, can contain the information enabling the image-captured time to be specified.

Further, the thickness information collecting unit 114 may, without calculating the average value of the thicknesses of the blood vessels of the veins, output all of the extracted thicknesses of the blood vessels of the veins to the determination unit 130.

Operational Example of Determination Unit

The determination unit 130 determines whether the captured image of the palm belongs to the authentication target user or not. Further, the determination unit 130 determines whether the captured image of the palm is of the living organism or not.

Figure 10:
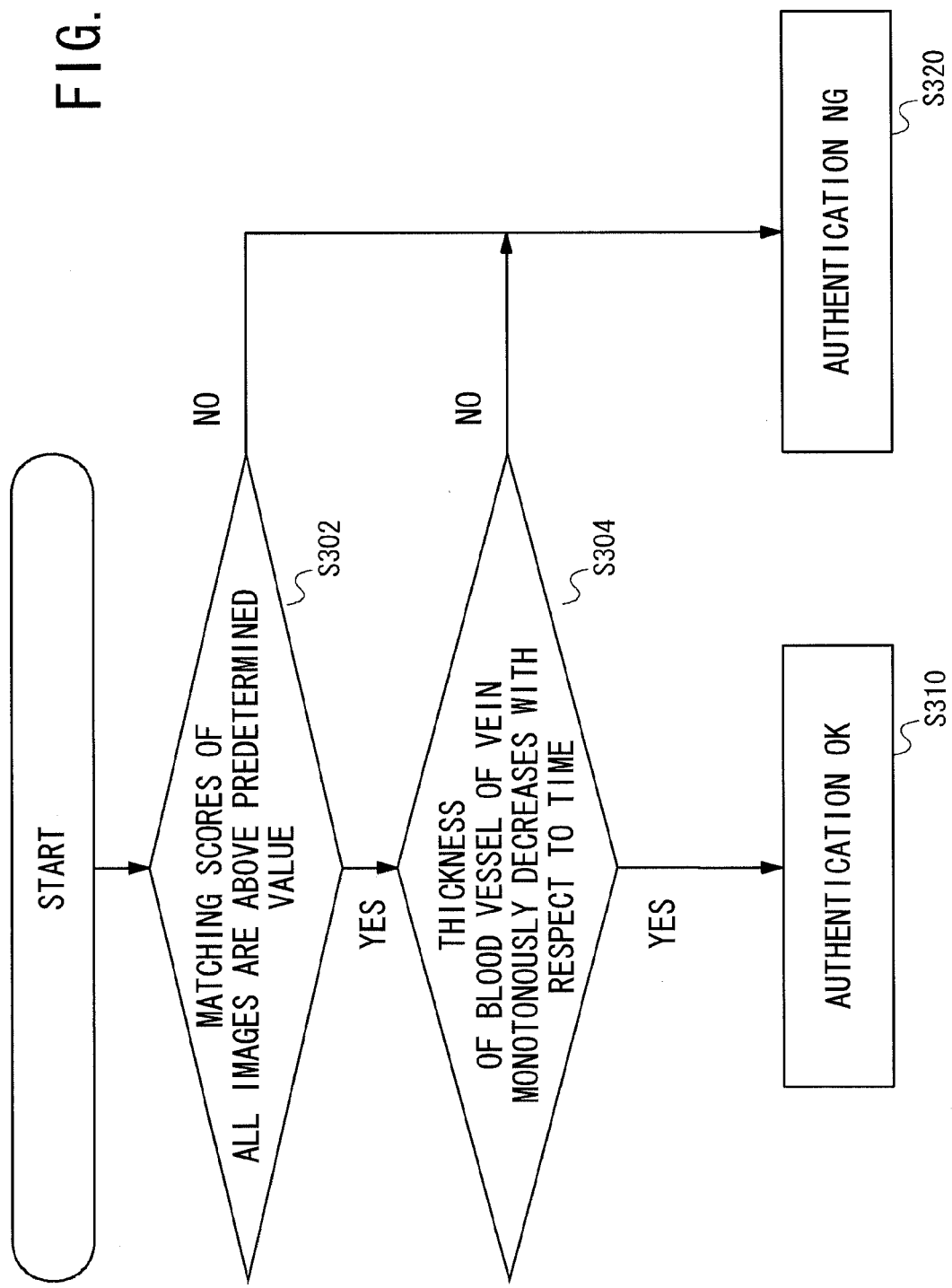
FIG. 10 is a flowchart showing an operational example of a determination unit.

FIG. 10 is a flowchart showing an operational example of the determination unit. The determination unit 130 receives the input of the matching score on the per-captured-image basis from the vein authentication unit 120. Moreover, the determination unit 130 receives the input of the average value of the thicknesses of the blood vessels of the veins on the per-captured-image basis from the liveness detection unit 110.

The determination unit 130 determines whether or not each of the matching scores of all of the captured images is equal to or larger than a predetermined value (S302). An implication of "the matching score being less than the predetermined value" is that the vein of the vein pattern data extracted from the storage unit 126 is different from the vein of the vein pattern information extracted from the captured image.

If each of the matching scores of all of the captured images is not equal to or larger than the predetermined value, i.e., if at least one matching score is less than the predetermined value (S302; NO), the determination unit 130 determines that the captured image does not belong to the user specified by the vein pattern data extracted from the storage unit 126, resulting in a failure in the authentication (authentication NG) (S320).

Whereas if each of the matching scores of all of the captured images is equal to or larger than the predetermined value (S302; YES), the operation proceeds to step S304.

The determination unit 130 determines whether or not the thickness of the blood vessel of the vein monotonously decreases with respect to the time (S304). An implication of "the thickness of the blood vessel of the vein monotonously decreasing with respect to the time is that the captured image is of the living organism.

The thickness of the blood vessel of the vein monotonously does not decrease with respect to the time, i.e., the thickness of the blood vessel of the vein increases at least temporarily or does not change at least temporarily with respect to the time (S302; NO), in which case the determination unit 130 determines that the captured image is not of the living organism, resulting in the failure in the authentication (authentication NG) (S320).

Whereas if the thickness of the blood vessel of the vein monotonously decreases with respect to the time (S302; YES), the determination unit 130 determines that the captured image is of the living organism, resulting in a success in authentication (authentication OK) (S310).

Herein, such a case is demonstrated that the vein sensor unit 102 is installed in the position higher than the operation unit 104, however, if the vein sensor unit 102 is installed in the position lower than the operation unit 104, the determination unit 130 determines whether or not the thickness of the blood vessel of the vein monotonously increases with respect to the time. This is because an implication of "the thickness of the blood vessel of the vein monotonously increasing with respect to the time" is that the captured image is of the living organism in this case.

Figure 11:
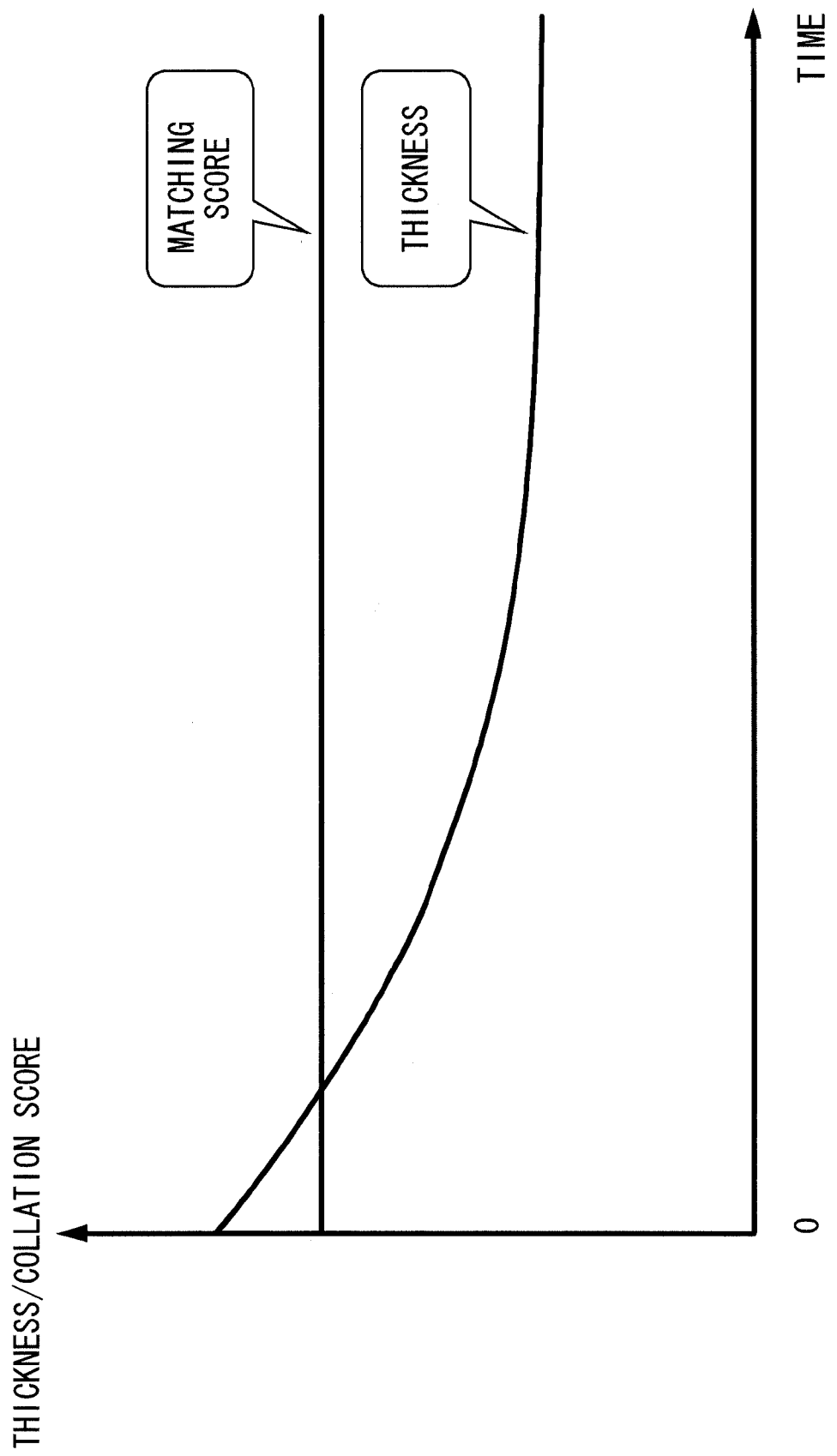
FIG. 11 is a diagram illustrating an example of a matching score and a time-based variation of a thickness of a blood vessel of the vein when a living organism is held properly.

First Example of Matching Score and Time-Based Variation of Thickness of Blood Vessel of Vein FIG. 11 is a diagram showing an example of the matching score and the time-based variation of the thickness of the vein when properly holding the living organism. In FIG. 11, the axis of abscissa represents the time, and the axis of ordinates represents the matching score or the thickness of the blood vessel of the vein.

In FIG. 11, it is assumed that the vein sensor unit 102 starts capturing the palm at the time 0 and the palm is captured at an interval of a predetermined period of time. The matching score takes a value equal to or larger than the predetermined value demonstrating an identity of the user specified by the vein pattern data extracted from the storage unit 126 but does not change with respect to time. On the other hand, the thickness of the blood vessel of the vein decreases monotonously with respect to the time because of becoming gradually thinner.

At this time, the determination unit 130 determines that the hand held over the vein sensor unit 102 is of the user specified by the vein pattern data extracted from the storage unit 126 and of the living organism, resulting in the success in authentication (authentication OK).

Figure 12:
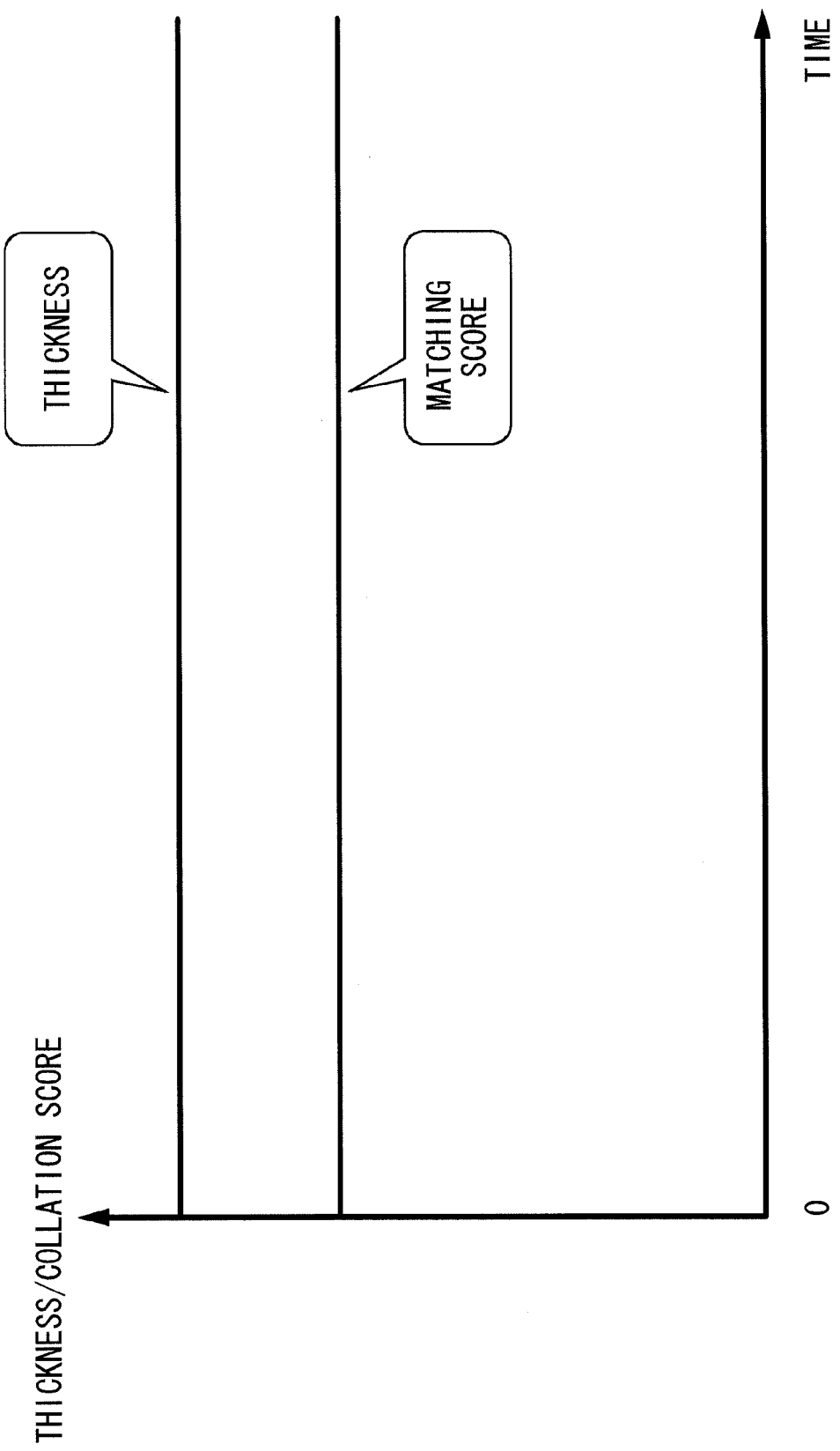
FIG. 12 is a diagram illustrating an example of the matching score and the time-based variation of the thickness of the blood vessel of the vein when a non-living organism is held.

Second Example of Matching Score and Time-Based Variation of Thickness of Blood Vessel of Vein FIG. 12 is a diagram showing an example of the matching score and the time-based variation of the thickness of the vein when holding the target body defined as the fake. A presumption herein is that a palm of a photo-based fake hand is held over the vein sensor unit 102. In FIG. 12, the axis of abscissa represents the time, and the axis of ordinates represents the matching score or the thickness of the blood vessel of the vein.

In FIG. 12, it is assumed that the vein sensor unit 102 starts capturing the target body at the time 0 and captures the target body at the interval of the predetermined time. It is also presumed that the matching score takes the value equal to or larger than the predetermined value demonstrating the identity of the user specified by the vein pattern data extracted from the storage unit 126. The matching score does not change with respect to the time. Further, the thickness of the blood vessel of the vein does not vary with respect to the time.

Hence, the matching score takes the value equal to or larger than the predetermined value, however, the thickness of the blood vessel of the vein does not vary. Therefore, the determination unit 130 determines that the hand held over the vein sensor unit 102 is not the living organism, resulting in the failure in authentication (authentication NG).

Figure 13:
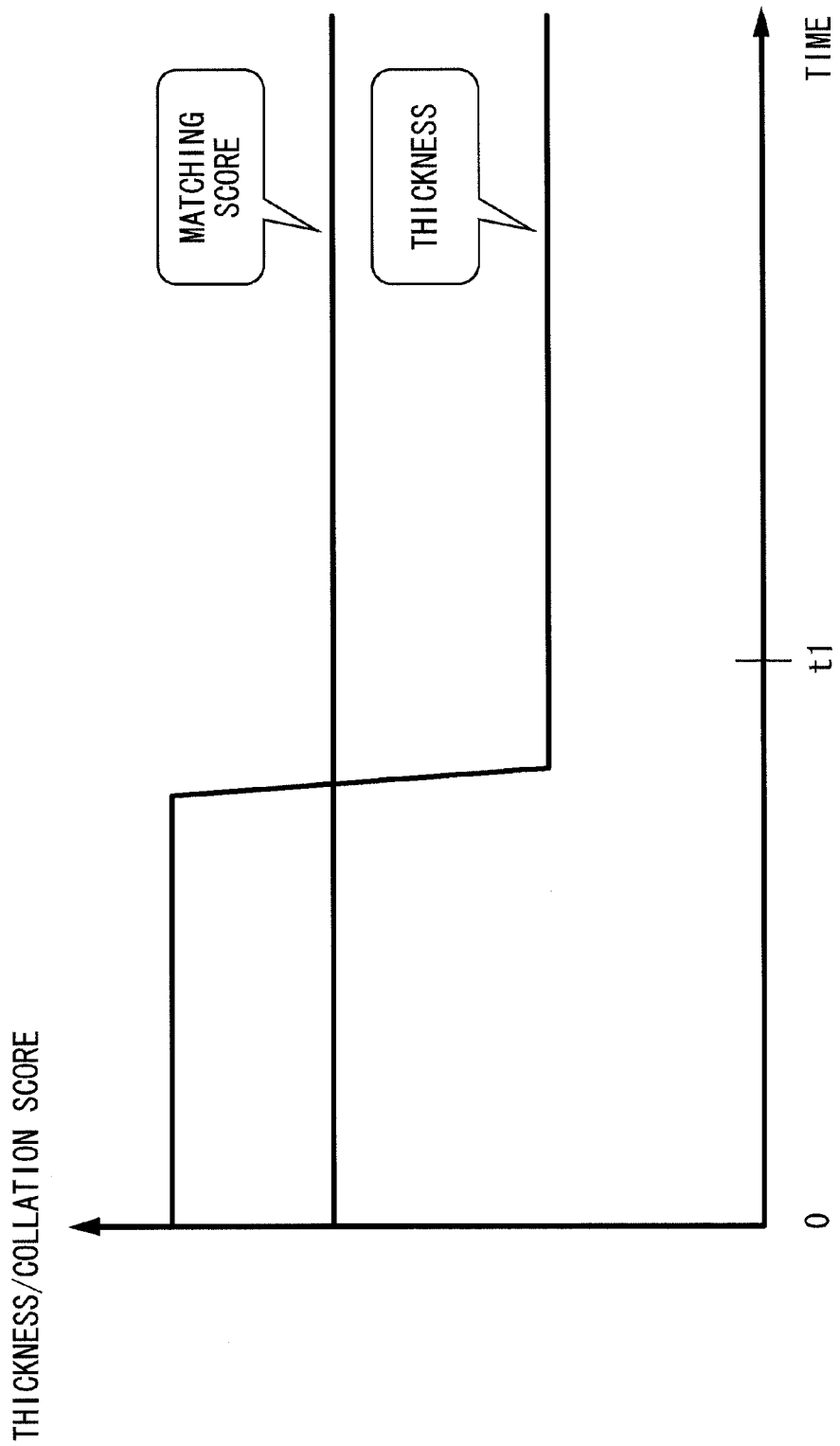
FIG. 13 is a diagram illustrating an example of the matching score and the time-based variation of the thickness of the blood vessel of the vein when the non-living organism is held.

Third Example of Matching Score and Time-Based Variation of Thickness of Blood Vessel of Vein FIG. 13 is a diagram showing another example of the matching score and the time-based variation of the thickness of the vein when holding the target body defined as the fake. A presumption herein is that the palm of the photo-based fake hand is held over the vein sensor unit 102 and another photo-based fake hand is held over the vein sensor unit 102 after the predetermined time. In FIG. 13, the axis of abscissa represents the time, and the axis of ordinates represents the matching score or the thickness of the blood vessel of the vein.

In FIG. 13, it is assumed that the vein sensor unit 102 starts capturing the target body at the time 0 and again captures the target body at the time t1. It is also presumed that the matching score takes the value equal to or larger than the predetermined value demonstrating the identity of the user specified by the vein pattern data extracted from the storage unit 126. The matching score does not change with respect to the time. The value of the thickness of the blood vessel of the vein that is captured at the time t1, but decreases in comparison with the value given when captured at the time 0. Hence, in the case of using the palm of the fake hand such as this, only the two captures taken at the time 0 and the time t1 have a possibility that the determination unit 130 makes the success-determination for the authentication (authentication OK).

The image count is increased by further shortening the capturing time interval of the vein sensor unit 102, thereby enabling the determination unit 130 to determine that the palm of the fake hand is not the living organism to result in the failure in authentication (authentication NG) even when using the palm of the fake hand. This is because of observing the region having no time-based variation of the thickness of the vein by shortening the capture time interval.

The thickness of the blood vessel of the vein is stabilized in 5-6 seconds after moving to the high position from the low position. Hence, it is preferable that the capturing is carried out at least three times or more for 5-6 seconds since the start of the capturing. Further, the variation of the thickness of the blood vessel of the vein rises immediately after the hand has been held over the vein sensor unit 102. Hence, preferably, the capturing may be performed at least three times or more for 2-3 seconds since the start of the capturing. The determination unit 130 is enabled to make a more precise determination as the capturing interval gets shorter and the capturing count becomes larger. It is desirable for reducing the time when the user is confined to the vein sensor unit 102 that the capturing time be shorter. Further, the vein sensor unit 102 is also capable of capturing a moving picture of the palm and taking out a static image at the interval of the predetermined time.

Measuring Point and Measuring Direction of Thickness of Blood Vessel of Vein

Figure 14:
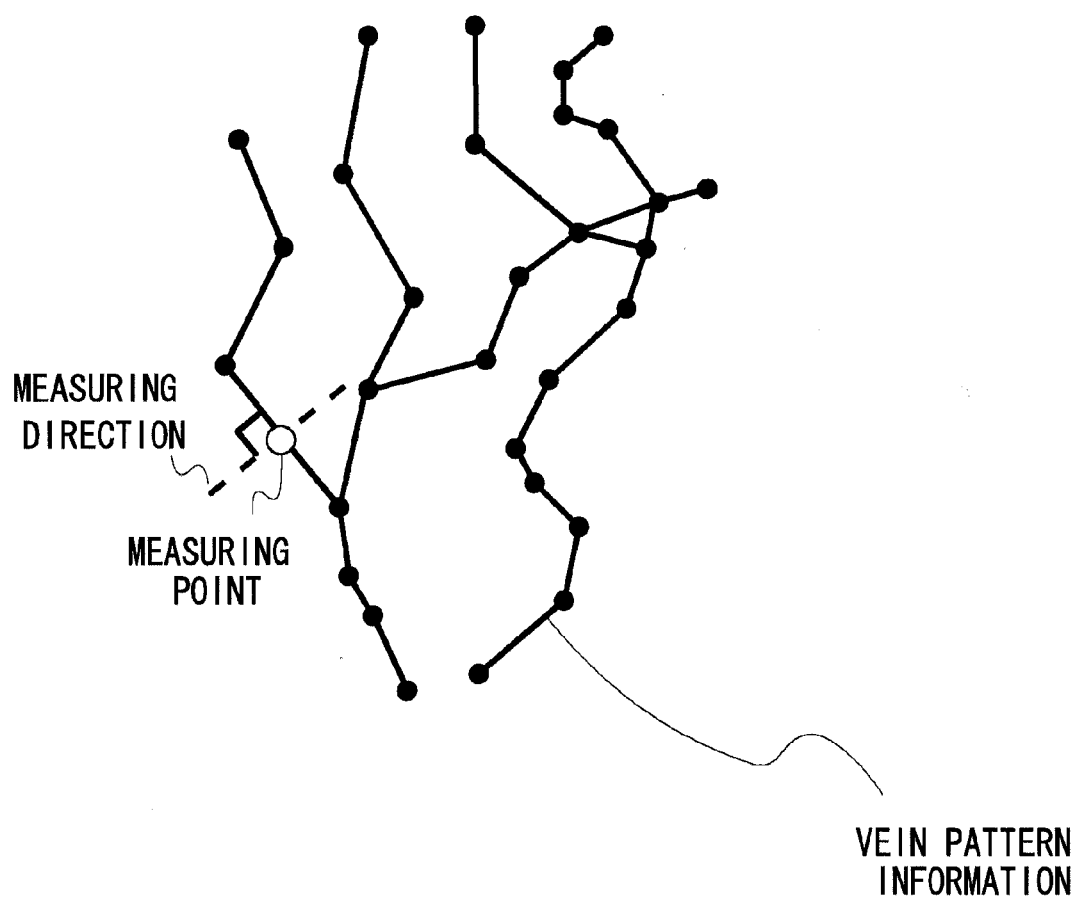
FIG. 14 is a diagram illustrating an example of a measuring point and a measuring direction of the thickness of the blood vessel of the vein.

FIG. 14 is a diagram showing an example of the measuring points and the measuring direction of the thickness of the blood vessel of the vein. In FIG. 14, the vein pattern information is depicted by points (solid black circles) and straight lines (solid lines) formed by connecting these points to each other.

As specified by a solid white circle in FIG. 14, the midpoint of the specified line segment partly configuring the vein pattern from the vein pattern information is determined as the measuring point of the thickness of the blood vessel of the vein. Moreover, as specified by a dotted line in FIG. 14, the direction passing through the measuring point and orthogonal to the direction of the line segment becomes the measuring direction for measuring the thickness of the blood vessel of the vein. A plurality of measuring points can be determined. The measuring point and the measuring direction of the thickness of the blood vessel of the vein may also be determined otherwise.

Calculation Method of Thickness of Blood Vessel of Vein

A calculation method of the thickness of the blood vessel of the vein is exemplified. The calculation method of the thickness of the blood vessel of the vein is not limited to a method given herein. The calculation method of the thickness of the blood vessel of the vein may involve utilizing other calculation methods.

Figure 15:
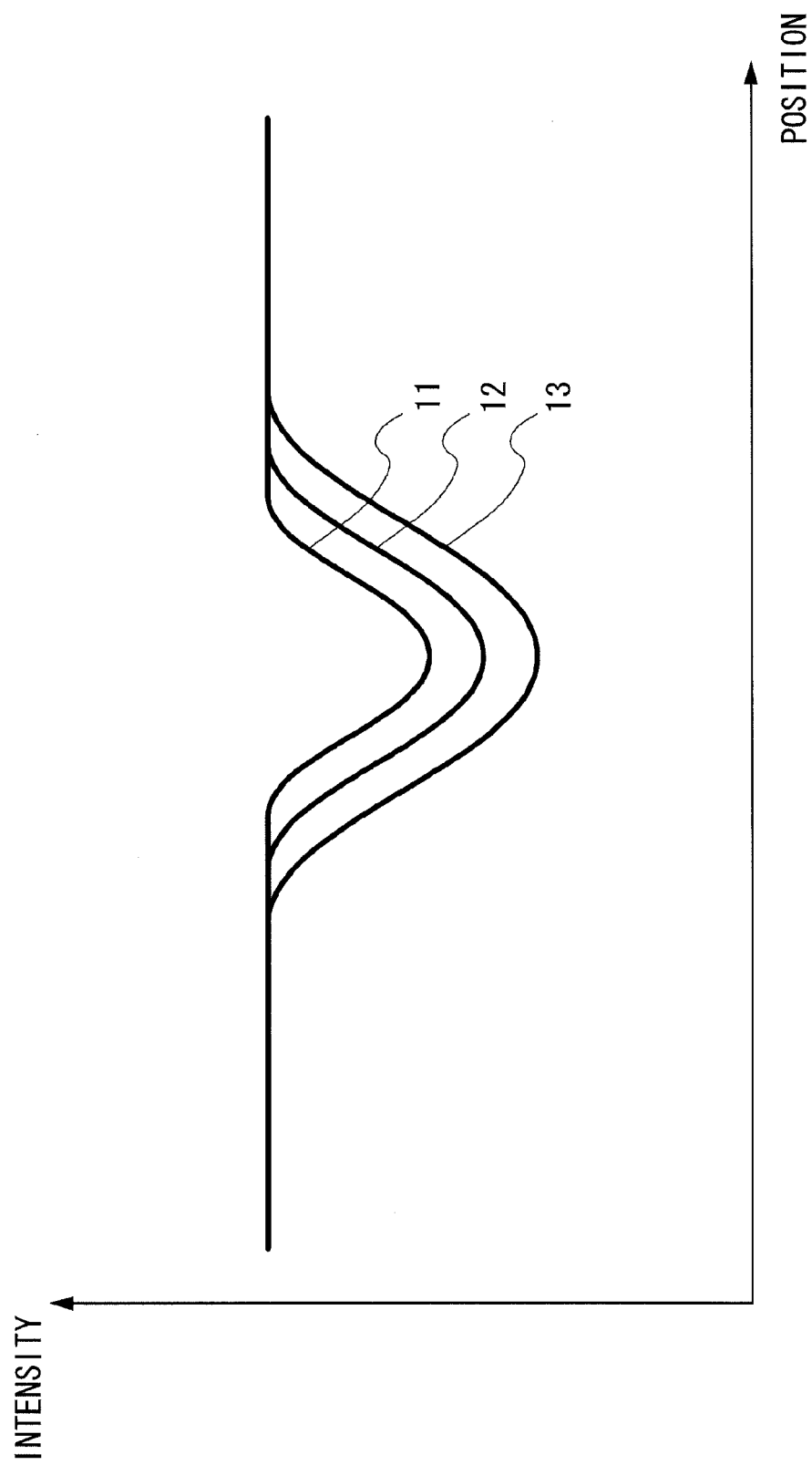
FIG. 15 is a diagram illustrating an example of a profile of intensity of a vein image.

FIG. 15 is a diagram showing an example of a profile of intensity of the vein image. FIG. 15 is the diagram depicting the intensity in the direction orthogonal to the direction of the blood vessel of the vein in the vein image with respect to the veins having the different thicknesses of the vein blood vessels. In the graph of FIG. 15, the axis of abscissa represents the position, and the axis of ordinates represents the intensity. FIG. 15 depicts the three veins (veins 11, 12, 13) in superposition by way of an example.

In the vein image, the vein appears dark. Namely, in the vein image, a region exhibiting the low intensity is a region where the vein exists. Further, as the thickness of the blood vessel of the vein increases, the intensity gets much lower. In the three veins depicted in FIG. 15, the intensity decreases in the sequence of the vein 11, the vein 12 and the vein 13. Hence, in the three veins depicted in FIG. 15, the vein 11 has the smallest thickness of the blood vessel, while the vein 13 has the largest thickness of the blood vessel. In vein curves in FIG. 15, a region exhibiting the high intensity but no variation in intensity with respect to the change in position is deemed to be the region including no existence of the vein.

Herein, the method of calculating the thickness of the blood vessel of the vein by utilizing the intensity information of the vein image will be described.

Calculation Based on Fixed Threshold Value

Figure 16:
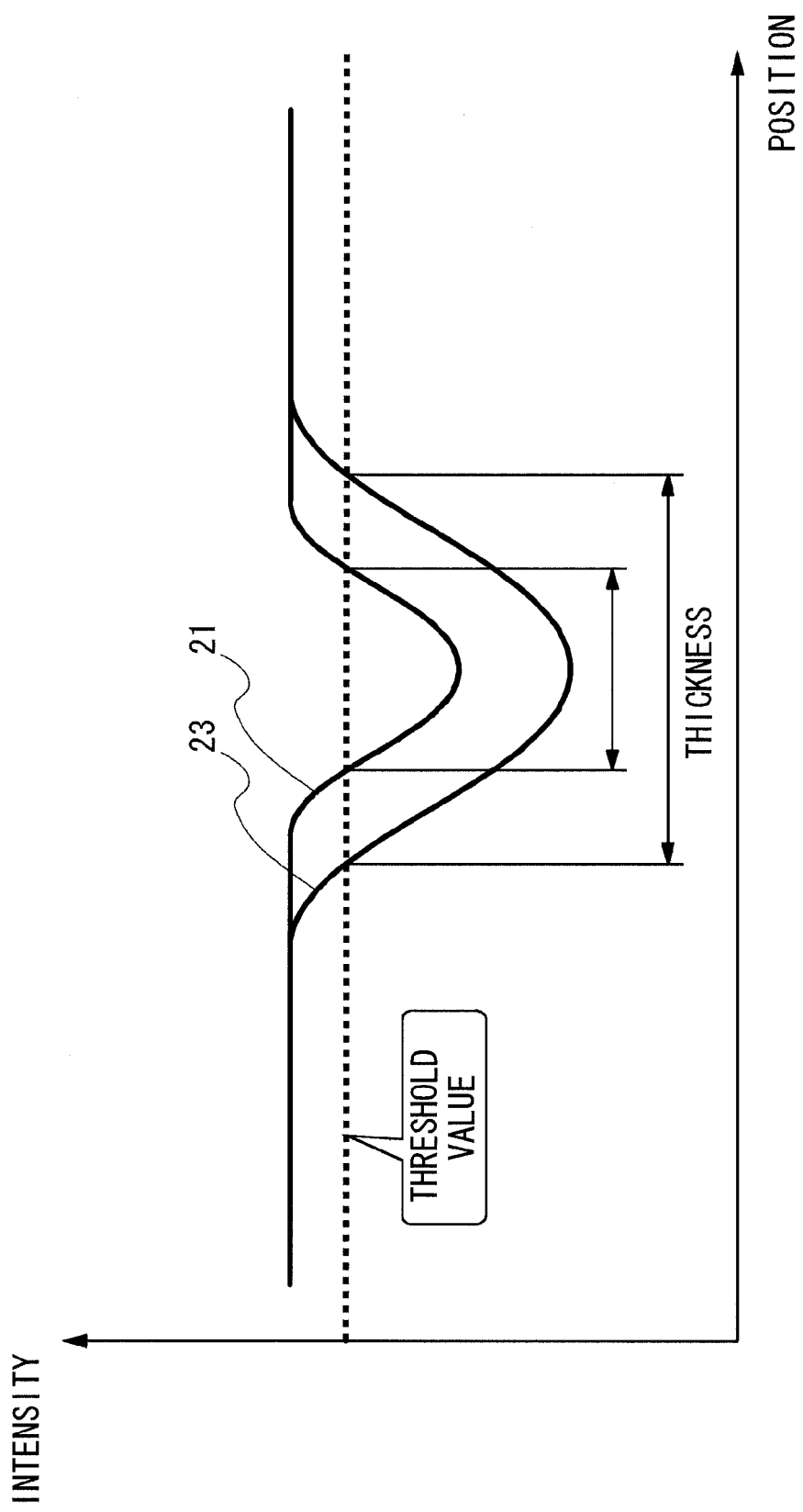
FIG. 16 is an explanatory diagram of a calculation method of the thickness of the blood vessel of the vein by use of a fixed threshold value.

FIG. 16 is an explanatory diagram of the calculation method of the thickness of the blood vessel of the vein on the basis of a fixed threshold value. Herein, the method of calculating the thickness of the blood vessel of the vein by utilizing the fixed threshold value, is described.

FIG. 16 is a diagram, similar to FIG. 15, illustrating the intensity in the direction orthogonal to the direction of the blood vessel of the vein in the vein image with respect to the veins having the different thicknesses of the vein blood vessels. FIG. 16 depicts the two veins (veins 21, 23) in superposition.

As in FIG. 16, a predetermined threshold value is set for the intensity. The predetermined threshold value to be set is a value lower than the value of the intensity of the region deemed not to be the vein. An assumption is that a region where the intensity is equal to or smaller than the predetermined threshold value is defined as the vein. Another assumption is that a length of the region is defined as the thickness of the blood vessel of the vein.

Calculation Based on Half Width

Figure 17:
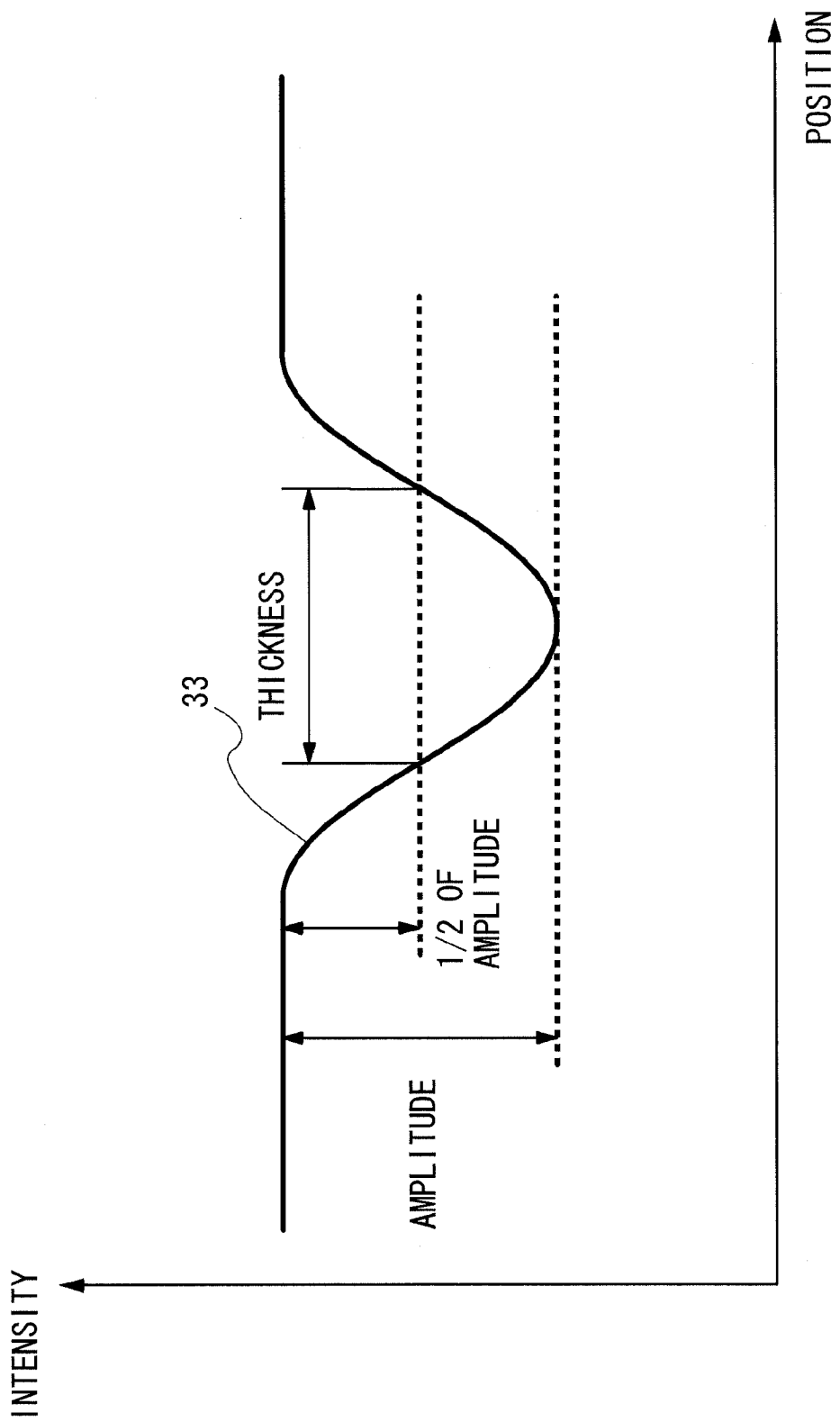
FIG. 17 is an explanatory diagram of the calculation method of the thickness of the blood vessel of the vein by use of a half width.

FIG. 17 is an explanatory diagram of the calculation method of the thickness of the blood vessel of the vein on the basis of a half width. FIG. 17 is a diagram, similar to FIG. 15, illustrating the intensity in the direction orthogonal to the direction of the blood vessel of the vein in the vein image with respect to the veins having the different thicknesses of the vein blood vessels.

As in FIG. 17, an amplitude is defined as a difference between the lowest value of the intensity of a vein 33 and a intensity value of a region deemed not to be the vein. A value obtained by subtracting a half-value of the amplitude from the intensity value of the region deemed not to be the vein, is set as a predetermined threshold value. An assumption is that a region where the intensity is equal to or smaller than the predetermined threshold value is defined as the vein. Another assumption is that a length of the region is defined as the half width. Still another assumption is that the length of the region is defined as the thickness of the blood vessel of the vein.

Calculation Based on Amplitude

FIG. 18 is an explanatory diagram of the calculation method of the thickness of the blood vessel of the vein on the basis of the amplitude. FIG. 18 is a diagram, similar to FIG. 15, illustrating the intensity in the direction orthogonal to the direction of the blood vessel of the vein in the vein image.

As in FIG. 18, the amplitude is defined as the difference between the lowest value of the intensity of a vein 43 and the intensity value of the region deemed not to be the vein. The amplitude can be deemed to be proportional to the thickness of the blood vessel of the vein. Hence, in the embodiment, the amplitude can be utilized as a substitute for the thickness of the blood vessel of the vein. Further, the thickness of the blood vessel of the vein may also be calculated in a manner that multiplies the amplitude by a predetermined coefficient.

Effects in Embodiment

According to the embodiment, the blood pressure of the hand and the thickness of the blood vessel of the vein can be artificially varied by installing the input unit which manually accepts the input and the vein sensor unit which captures the hand in the different positions. According to the embodiment, it is feasible to determine, whether the target body is the living organism or not, by observing the time-based variation of the thickness of the vein. Moreover, according to the embodiment, the thickness of the blood vessel of the vein can be properly measured by approximately correcting the information on the detected thickness of the blood vessel of the vein.

According to the embodiment, it is feasible to simultaneously execute the vein authentication of the palm of the captured hand and the liveness detection as to whether the palm of the captured hand is the living organism or not. Hence, the target body in the vein authentication must be identical with the target body in the liveness detection, thereby disabling swap-based arrogation from being done. Further, it is highly difficult to produce a fake showing a dynamic change in thickness of the blood vessel of the vein, resulting in difficulty of doing an unauthorized act by spoofing.

According to the configuration in the embodiment, the vein authentication and the liveness detection can be performed for the same period of time as in the case of only the vein authentication. Therefore, in the embodiment, though the vein authentication and the liveness detection are carried out, a load on the user does not largely increase as compared with the case of performing only the vein authentication.

According to the embodiment, the matching result of the vein is normal, and the capturing target is the living organism, in which case the authentication accuracy can be escalated by authenticating the user.

What is claimed is:

1. A biometric authentication device, comprising:
   an operation panel configured to input identifying information of a user;
   a camera configured capture an image of a user's hand a plural number of times; and
   one or more processors configured to:
   extract vein information, on a per image basis, of the hand image captured by the camera and execute a matching process of matching the vein information with previously-provided vein data associated with the identifying information;
   acquire determination data specifying, based on a thickness of a vein in a predetermined position in the hand image, whether the hand image is acquired by capturing a living organism or not; and
   authenticate the user when a matching result of the matching on the per hand-image basis demonstrates its normality and the determination data demonstrates that the hand image is acquired by capturing the living organism, or does not authenticate the user.

2. The biometric authentication device according to claim 1, wherein the one or more processors are further configured to measure the thickness of the vein in the predetermined position on the per hand-image basis, and
   authenticate the user when the matching result of the matching on the per hand-image basis demonstrates its normality and the thickness of the vein in the predetermined position that is measured by the measuring shows a time-based variation between the hand images, or does not authenticate the user.

3. The biometric authentication device according to claim 2, wherein the operation panel and the camera are installed with different heights so that a height of the user's hand differs when the user operates the operation panel and when the image is captured by the camera, and
   the camera executes the capturing as triggered by inputting the identifying information of the user.

4. The biometric authentication device according to claim 2, wherein the one or more processors are further configured to correct the vein thickness acquired from the hand image on the basis of the vein data.

5. A biometric authentication method, comprising:
   accepting an input of identifying information of a user;
   capturing an image of a user's hand a plural number of times;
   extracting vein information, on a per image basis, of the hand image captured in the capturing and executing matching the vein information with previously-provided vein data associated with the identifying information;
   acquiring determination data specifying, based on a thickness of a vein in a predetermined position in the hand image, whether the hand image is acquired by capturing the living organism or not; and
   authenticating the user when a matching result in the matching step on the per hand-image basis demonstrates its normality and the determination data demonstrates that the hand image is acquired by capturing the living organism, or not authenticating the user.

6. The biometric authentication method according to claim 5, further comprising measuring the thickness of the vein in the predetermined position on the per hand-image basis, and
   the determining includes authenticating the user when the matching result in the matching on the per hand-image basis demonstrates its normality and the thickness of the vein in the predetermined position that is measured in the measuring shows a time-based variation between the hand images, or not authenticating the user.

7. The biometric authentication method according to claim 6, wherein the capturing includes capturing the hand image of the user by a camera installed with a height different from an operation panel to accept an input of the identifying information from the user, and
   the capturing is executed as triggered by inputting the identifying information of the user.

8. The biometric authentication method according to claim 6, further comprising correcting the vein thickness acquired from the hand image on the basis of the vein data.

9. A biometric authentication device, comprising:
an operation panel configured to input identifying information of a user;
a camera configured to capture an image of a user's hand; and
one or more processors configured to:
extract vein information of the hand image captured by the camera and execute matching the vein information with previously-provided vein data associated with the identifying information;
measure a thickness of a vein in a predetermined position on hand images each of which is captured on different time; and
authenticate the user when a matching result of the matching on the per hand-image basis demonstrates its normality and the thickness of the vein in the predetermined position shows a time-based variation between the hand images.

* * * * *

UNITED STATES PATENT AND TRADEMARK OFFICE
CERTIFICATE OF CORRECTION

PATENT NO. : 8,948,464 B2
APPLICATION NO. : 13/160919
DATED : February 3, 2015
INVENTOR(S) : Hama et al.

It is certified that error appears in the above-identified patent and that said Letters Patent is hereby corrected as shown below:

In the Claims

Claim 1, Column 15, Line 60:

after "configured" insert --to--, therefor.

Claim 5, Column 16, Line 32:

delete "method," and insert --method--, therefor.

Signed and Sealed this
Thirtieth Day of June, 2015

Michelle K. Lee
*Director of the United States Patent and Trademark Office*